(12) United States Patent
Gohno et al.

(10) Patent No.: US 7,639,776 B2
(45) Date of Patent: Dec. 29, 2009

(54) X-RAY CT APPARATUS

(75) Inventors: Makoto Gohno, Tokyo (JP); Tetsuya Horiuchi, Tokyo (JP); Akihiko Nishide, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 210 days.

(21) Appl. No.: 11/757,732

(22) Filed: Jun. 4, 2007

(65) Prior Publication Data
US 2007/0286332 A1  Dec. 13, 2007

(30) Foreign Application Priority Data
Jun. 9, 2006  (JP) ............................... 2006-161245

(51) Int. Cl.
*A61B 6/00* (2006.01)
(52) U.S. Cl. ............................... 378/15; 378/4; 378/109
(58) Field of Classification Search .................... 378/4, 378/15, 16
See application file for complete search history.

(56) References Cited

U.S. PATENT DOCUMENTS

| | | | | |
|---|---|---|---|---|
| 5,301,108 | A * | 4/1994 | Hsieh | 378/8 |
| 5,379,333 | A * | 1/1995 | Toth | 378/16 |
| 5,400,378 | A * | 3/1995 | Toth | 378/16 |
| 5,450,462 | A * | 9/1995 | Toth et al. | 378/16 |
| 5,568,530 | A * | 10/1996 | Saito et al. | 378/4 |
| 5,696,807 | A * | 12/1997 | Hsieh | 378/109 |
| 6,198,789 | B1 * | 3/2001 | Dafni | 378/8 |
| 6,285,741 | B1 * | 9/2001 | Ackelsberg et al. | 378/110 |
| 6,404,844 | B1 | 6/2002 | Horiuchi et al. | |

(Continued)

FOREIGN PATENT DOCUMENTS

EP  1172069 A1  1/2002

(Continued)

OTHER PUBLICATIONS

Hiroyuki Kudo et al., Exact and approximate algorithms for helical cone-beam CT, Physics in Medicine and Biology, Jul. 7, 2004, pp. 2913-2931, London, GB.

*Primary Examiner*—Allen C. Ho
*Assistant Examiner*—Alexander H Taningco
(74) *Attorney, Agent, or Firm*—Armstrong Teasdale LLP

(57) ABSTRACT

The present invention aims to obtain a tomographic image similar in image quality to a tomographic image obtained by executing a scan at X-ray tube current value set by an X-ray automatic exposure function even when the X-ray tube current value set by the X-ray automatic exposure function are not within a standard range of the X-ray tube current values settable at the X-ray tube (21). X-ray tube current value supplied to the X-ray tube (21) are set by the X-ray automatic exposure function. Thereafter, when the X-ray tube current value set by the X-ray automatic exposure function is not within in the standard range of the X-ray tube current value settable at the X-ray tube, the X-ray tube current value at a portion not within the standard range are changed so as to be within the standard range, and the set value of helical pitch is changed so as to correspond to the ratio between the pre-changed x-ray tube current value and the post-changed X-ray tube current value.

21 Claims, 21 Drawing Sheets

U.S. PATENT DOCUMENTS

| | | | |
|---|---|---|---|
| 6,459,756 B1 * | 10/2002 | Tam et al. | 378/15 |
| 6,507,639 B1 * | 1/2003 | Popescu | 378/108 |
| 6,529,575 B1 | 3/2003 | Hsieh | |
| 6,529,576 B2 * | 3/2003 | Hsieh et al. | 378/15 |
| 6,639,965 B1 * | 10/2003 | Hsieh et al. | 378/8 |
| 6,744,846 B2 * | 6/2004 | Popescu et al. | 378/16 |
| 6,836,535 B2 * | 12/2004 | Toth et al. | 378/159 |
| 6,901,129 B2 * | 5/2005 | Tachizaki et al. | 378/4 |
| 6,904,127 B2 * | 6/2005 | Toth et al. | 378/110 |
| 7,050,532 B2 | 5/2006 | Gohno | |
| 7,054,407 B1 | 5/2006 | Li et al. | |
| 2003/0123603 A1 | 7/2003 | Suzuki | |
| 2004/0202277 A1 | 10/2004 | Okumura et al. | |
| 2004/0202283 A1 | 10/2004 | Okumura et al. | |
| 2004/0264628 A1 | 12/2004 | Besson | |
| 2005/0053190 A1 * | 3/2005 | Gohno | 378/16 |
| 2005/0249329 A1 | 11/2005 | Kazama et al. | |
| 2006/0109954 A1 | 5/2006 | Gohno | |
| 2007/0071160 A1 | 3/2007 | Nishide et al. | |

FOREIGN PATENT DOCUMENTS

| | | |
|---|---|---|
| JP | 2001-178713 | 7/2001 |
| JP | 2003010168 | 1/2003 |
| JP | 2003116836 | 4/2003 |
| JP | 2004000585 | 1/2004 |
| JP | 2004132859 | 4/2004 |
| JP | 2006110183 | 4/2006 |
| WO | 0211068 A1 | 2/2002 |
| WO | 2004071301 A1 | 8/2004 |
| WO | 2004080309 A2 | 9/2004 |
| WO | 2006006090 A1 | 1/2006 |

* cited by examiner

Step S2

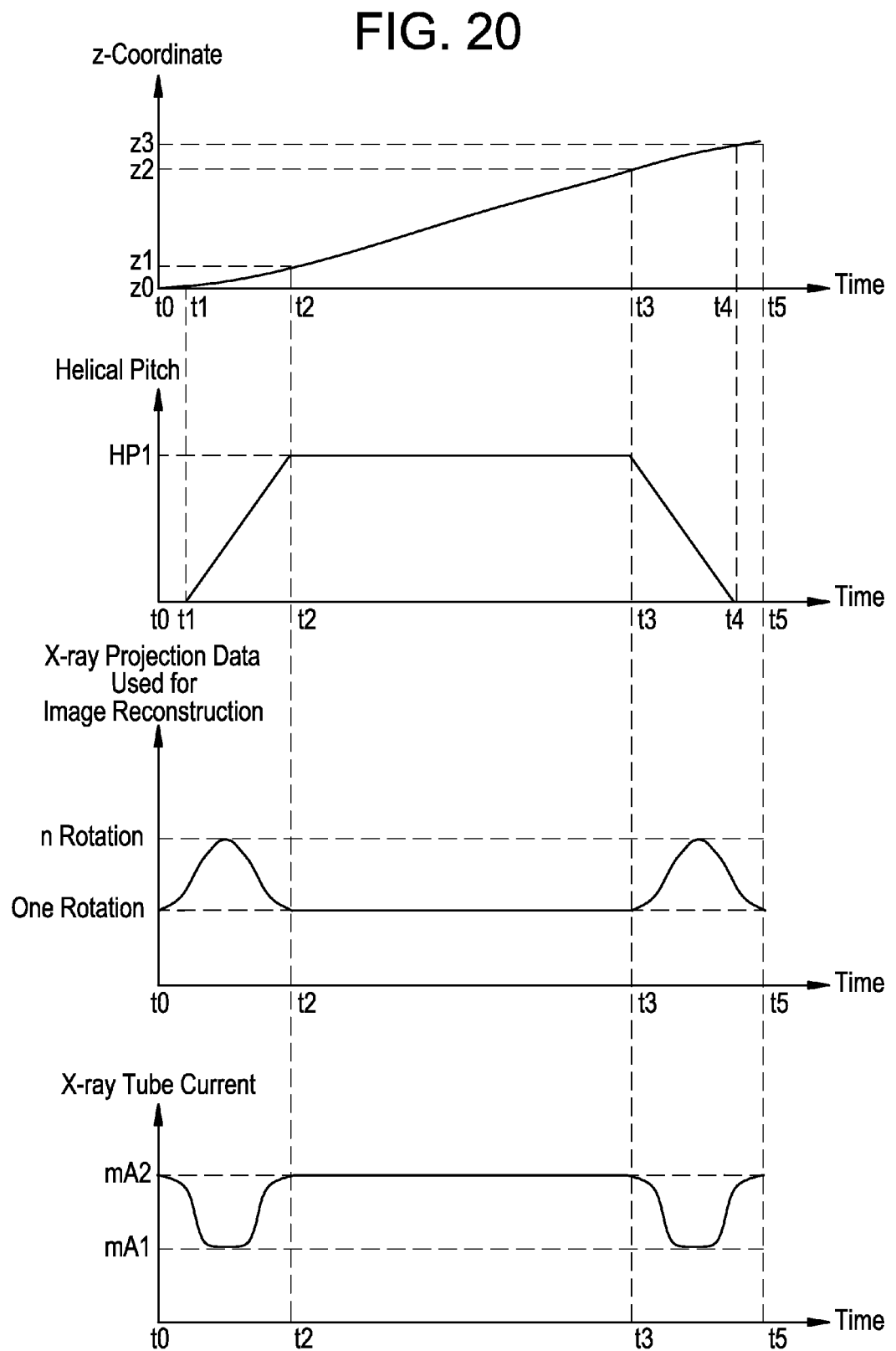

X-RAY CT APPARATUS

CROSS REFERENCE TO RELATED APPLICATIONS

This application claims the benefit of Japanese Patent Application No. 2006-161245 filed Jun. 9, 2006.

BACKGROUND OF THE INVENTION

The present invention relates to a medical X-ray CT (Computed Tomography) apparatus, and to an X-ray CT apparatus which realizes a reduction in exposure and an improvement in image quality using an X-ray automatic exposure function upon a conventional scan (axial scan), a cine scan, a helical scan, a parameter-pitch helical scan or a helical shuttle scan.

An X-ray CT apparatus having a multi-row X-ray detector or a two-dimensional X-ray area detector of a matrix structure typified by a flat panel has heretofore realized a reduction in exposure and an improvement in image quality using an X-ray automatic exposure function (corresponding to a function called "auto milliampere" or the like) (refer to, for example, Japanese Unexamined Patent Publication No. 2001-178713).

Here, the term "X-ray automatic exposure function" is called as a function for automatically setting an X-ray tube current condition for the irradiation of X-rays to a subject corresponding to a irradiation position so as to uniform image quality characteristic value typified by a standard deviation of a CT value at a tomographic image continuous in a z-direction.

For example, the X-ray CT apparatus optimizes a set value of an X-ray tube current supplied to an X-ray tube while scanning so as to meet a sectional area (profile area) at each z-direction position, of the subject, and optimizes a set value of an X-ray tube current at the time that a data acquisition system is rotated once upon photography, so as to meet a flat degree or aspect ratio of the shape of the subject in an xy plane, thereby realizing a reduction in exposure and an improvement in image quality.

Described specifically, a scout scan is executed on a subject before execution of an actual scan for the subject to thereby image or photograph a scout image corresponding to a fluoroscopical image of the subject. Thereafter, a central processing unit calculates and sets respective tube current values supplied to the X-ray tube, based on the photographed scout image, at respective positions where upon execution of the actual scan, X-rays are applied in a body-axis direction of the subject and a view direction respectively and the X-rays transmitted through the subject are detected thereby to obtain X-ray projection data. Here, the central processing unit determines, based on the scout image, sectional areas of the subject and sectional shapes thereof so as to adapt to the respective positions for obtaining the X-ray projection data at the periphery of the subject upon execution of the actual scan. Thereafter, the central processing unit adjusts and sets respective set values of tube currents at the respective positions so as to adapt to the sectional areas and sectional shapes determined at the respective positions. Then, the set tube current values are supplied to the X-ray tube and the actual scan is executed on the subject to acquire X-ray projection data of the subject. Thereafter, a tomographic image of the subject is image-reconstructed based on the so-obtained projection data.

FIGS. 16(a), 16(b), 16(c) and 16(d) respectively show changes in X-ray tube current set upon execution of a helical scan. Here, the horizontal axis indicates a z-direction coordinate, and the vertical axis indicates an X-ray tube current value.

In FIG. 16(a), an X-ray tube current having a constant value is supplied to an X-ray tube to image or photograph respective portions or regions of a subject as viewed in a z-direction. In this case, there might be case in which the exposure of excessive X-rays occurs in the case of a region small in sectional area and in the case where a subject is child.

Therefore, as shown in FIG. 16(c), profile areas of the subject at respective z-direction positions are determined based on a scout image to take into consideration the sectional area of the subject in the z-direction. Thereafter, the set value of the X-ray tube current is optimized based on the determined profile areas such that image noise (standard deviation of CT value at each pixel) becomes approximately constant in the z-direction at each tomographic image.

Incidentally, in this case, the image noise of each tomographic image is set as a noise index value by inputting set values onto an input screen as shown in FIG. 14, for example.

The section of the subject is flat whose vertical and horizontal directions are not identical in length as in a round shape and whose aspect ratio differs. Therefore, when the center lines of the X-ray tube and multi-row X-ray detector are placed in the vicinity of the x-axis direction where a subject having a section of an elliptical shape long in an x-axis direction is photographed as shown in FIG. 16(b), X-ray tube current values are set larger than X-ray tube current values necessary in the case of a circular shape having the same area as the elliptical shape. On the other hand, when the center lines of the X-ray tube and multi-row X-ray detector are placed in the vicinity of the y-axis direction, X-ray tube current values are set smaller than X-ray tube current values necessary in the case of a circular shape having the same area as the elliptical shape. Thus, the X-ray tube current is changed continuously within view angles corresponding to 360°, whereby image noise contained in X-ray projection data in each view direction becomes approximately constant in each view direction of the subject.

That is, the X-ray tube current values are optimized in the z-direction as shown in FIG. 16(c), and the X-ray tube current values are optimized even within the xy plane as shown in FIG. 16(b), whereby the X-ray tube current values optimized based on three-dimensional information in the x, y and z-directions of the subject are set as shown in FIG. 16(d), thereby realizing an improvement in image quality.

However, for example, in the case when the subject is large, each tomographic image is thin in slice thickness, a scan speed is fast or a noise index value is small and good image quality is required, and so on, each X-ray tube current value set in the above-described manner becomes larger. Therefore, when an X-ray tube which is small in thermal capacity and needs to be cooled when a large X-ray tube current is outputted for long hours, or an X-ray tube which cannot output a large X-ray tube current, are mounted in the X-ray CT apparatus, there might be a case in which it is not possible to adapt to the set X-ray tube current values.

Thus, in such a case, there might be a case in which the above X-ray automatic exposure function cannot fulfill its full function.

In the X-ray CT apparatus including the multi-row X-ray detector or the two-dimensional X-ray area detector typified by the flat panel, the problem of X-ray needless exposure shows more increasing tendency. There has been a further demand for optimization of the image quality of each tomographic image due to the X-ray automatic exposure function.

Therefore, an object of the present invention is to provide an X-ray CT apparatus which adjusts other imaging or scanning condition parameters without depending on a restriction on a tube current value of an X-ray tube even though the tube current value is limited, thereby realizing image quality of a tomographic image corresponding to the optimum noise standard value at an X-ray automatic exposure function.

Another object of the present invention is to provide an X-ray CT apparatus which assigns priorities to plural parameters for imaging or scanning conditions influencing each photographed tomographic image and adjusts the plural parameters influencing the photographed tomographic image in order based on the priorities, thereby making it possible to realize the optimum image quality at an X-ray automatic exposure function.

SUMMARY OF THE INVENTION

An X-ray CT apparatus according to a first aspect comprising X-ray data acquisition device for acquiring X-ray projection data by performing a scan, which X-rays being irradiated to a subject from a X-ray tube and the X-rays being transmitted through the subject by a X-ray detector, while the X-ray tube and the X-ray detector opposed to the X-ray tube being rotated around the subject on an axis of a direction extending along a z-direction, that is a body axis direction; image reconstructing device for image-reconstructing the X-ray projection data acquired by the X-ray data acquisition device to obtain a tomographic image; and imaging or scanning condition setting device for setting parameters of two kinds or more including X-ray tube current value as a condition for obtaining the tomographic image, wherein the imaging or scanning condition setting device include setting device for setting, in at least partial irradiation area, at least one of parameter other than the X-ray tube current value, to a desired value corresponding to an X-ray irradiation position, as a parameter for controlling image quality of the tomographic image.

In the X-ray CT apparatus according to the first aspect, parameters for imaging or scanning conditions, which influence a noise index value, can be adjusted. It is therefore possible to realize image quality which satisfies a noise index value of a tomographic image continuous in the z-direction.

There is provided an X-ray CT apparatus according to a second aspect, wherein in the X-ray CT apparatus described in the first aspect, said setting device sets a X-ray tube current value constant in an area in which at least one of the parameters other than the X-ray tube current value is set to the desired value corresponding to the X-ray irradiation position.

In the X-ray CT apparatus according to the second aspect, parameters for imaging or scanning conditions influencing a noise index value, other than the X-ray tube current values can be adjusted even when an X-ray tube current must be set as a constant value. It is therefore possible to realize image quality that satisfies a noise index value of each tomographic image continuous in the z-direction.

There is provided an X-ray CT apparatus according to a third aspect, wherein in the X-ray CT apparatus described in the first or second aspect, said setting device sets an X-ray tube current value to be smaller than a X-ray tube current value adjusted preferentially to obtain a desired image quality characteristic, in an area in which at least one of parameters other than the X-ray tube current value is set to the desired value corresponding to the X-ray irradiation position.

In the X-ray CT apparatus according to the third aspect, when, for example, each of X-ray tube current values determined by an X-ray automatic exposure function so as to make image quality constant in the z-direction, based on the noise index value or image quality index value set by the imaging or scanning condition setting device, falls outside a range of an X-ray tube current settable at the X-ray tube, the X-ray tube current value is set as a value smaller than the X-ray tube current settable at the X-ray tube, and each parameter for an imaging or scanning condition, other than the X-ray tube current values, which influences the noise index value, can be adjusted. It is therefore possible to realize image quality that satisfies a noise index value of each tomographic image continuous in the z-direction.

There is provided an X-ray CT apparatus according to a fourth aspect, wherein in the X-ray CT apparatus described in the first or second aspect, said setting device sets an X-ray tube current value to a value accompanied with a parameter set to the desired value in an area in which at least one of parameters other than the X-ray tube current value is set to the desired value corresponding to the X-ray irradiation position.

In the X-ray CT apparatus according to the fourth aspect, each parameter other than the X-ray tube current values is controlled and each X-ray tube current value is also set as a value determined by an X-ray automatic exposure function so as make image quality constant in the z-direction, based on the noise index value or image quality index value set by the imaging or scanning condition setting device. It is therefore possible to realize image quality that satisfies a noise index value of each tomographic image continuous in the z-direction.

There is provided an X-ray CT apparatus according to a fifth aspect, wherein in the X-ray CT apparatus described in the first aspect, said setting device sets at least one of parameters other than the X-ray tube current value to the desired value corresponding to the X-ray irradiation position according to the speed of traveling of the subject in z-direction.

In the X-ray CT apparatus according to the fifth aspect, when, for example, the speed of traveling of the table is changed during the scan as in a helical shuttle scan or a variable-pitch helical scan, each parameter for an imaging or scanning condition, other than the X-ray tube current values, which influences a noise index value, can be adjusted. It is therefore possible to realize image quality that satisfies a noise index value of each tomographic image continuous in the z-direction.

There is provided an X-ray CT apparatus according to a sixth aspect, wherein in the X-ray CT apparatus described in any of the first to fifth aspects, said parameter other than the X-ray tube current value which is set to the desired value corresponding to the X-ray irradiation positions includes distance between coordinate positions in the direction of the body axis of the subject of an axial scan, a cine scan or a helical scan.

In the X-ray CT apparatus according to the sixth aspect, each coordinate position (for example, helical pitch at helical scan) in the body-axis direction of the subject can be controlled as a parameter other than the X-ray tube current values. It is therefore possible to realize image quality that satisfies a noise index value of each tomographic image continuous in the z-direction even when the value of the X-ray tube current is limited.

There is provided an X-ray CT apparatus according to a seventh aspect, wherein said parameter other than the X-ray tube current value which is set to the desired value corresponding to the X-ray irradiation positions includes a parameter in use for an image space z-direction filtering process used in the image reconstructing device.

In the X-ray CT apparatus according to the seventh aspect, each of the parameters used for the image space z-direction filtering process used in the image reconstructing device can be controlled as the parameter other than the X-ray tube current values. It is therefore possible to realize image quality that satisfies a noise index value of each tomographic image continuous in the z-direction even when the value of the X-ray tube current is limited.

There is provided an X-ray CT apparatus according to an eighth aspect, wherein in the X-ray CT apparatus described in any of the first to fifth aspects, said parameter other than the X-ray tube current value which is set to the desired value corresponding to the X-ray irradiation positions includes a parameter in use for a projection data space row-direction filtering process used in the image reconstructing device.

In the X-ray CT apparatus according to the eighth aspect, each of the parameters used for the projection data space row-direction filtering process used in the image reconstructing device can be controlled as the parameter other than the X-ray tube current values. It is therefore possible to realize image quality that satisfies a noise index value of each tomographic image continuous in the z-direction even when the value of the X-ray tube current is limited.

There is provided an X-ray CT apparatus according to a ninth aspect, wherein in the X-ray CT apparatus described in any of the first to fifth aspects, said parameter other than the X-ray tube current value which is set to the desired value corresponding to the X-ray irradiation positions includes a parameter in use for a projection data space channel-direction filtering process used in the image reconstructing device.

In the X-ray CT apparatus according to the ninth aspect, each of the parameters used for the projection data space channel-direction filtering process used in the image reconstructing device can be controlled as the parameter other than the X-ray tube current values. It is therefore possible to realize image quality that satisfies a noise index value of each tomographic image continuous in the z-direction even when the value of the X-ray tube current is limited.

There is provided an X-ray CT apparatus according to a tenth aspect, wherein said parameter other than the X-ray tube current value which is set to the desired value corresponding to the X-ray irradiation positions includes a parameter in use for a projection data space view-direction filtering process used in the image reconstructing device.

In the X-ray CT apparatus according to the tenth aspect, each of the parameters used for the projection data space view-direction filtering process used in the image reconstructing device can be controlled as the parameter other than the X-ray tube current values. It is therefore possible to realize image quality that satisfies a noise index value of each tomographic image continuous in the z-direction even when the value of the X-ray tube current is limited.

There is provided an X-ray CT apparatus according to an eleventh aspect, wherein in the X-ray CT apparatus described in any of the first to fifth aspects, said parameter other than the X-ray tube current value which is set to the desired value corresponding to the X-ray irradiation positions includes an image reconstruction parameter used in the image reconstructing device.

In the X-ray CT apparatus according to the eleventh aspect, the image reconstruction parameter (for example, the amount of projection data used in the image reconstruction) used in the image reconstructing device can be controlled as the parameter other than the X-ray tube current values. It is therefore possible to realize image quality that satisfies a noise index value of each tomographic image continuous in the z-direction even when the value of the X-ray tube current is limited.

There is provided an X-ray CT apparatus according to a twelfth aspect, wherein in the X-ray CT apparatus described in any of the first to eleventh aspects, said parameters of the two or more parameters set to the desired value corresponding to the X-ray irradiation position are set with priorities being assigned thereto in said setting device.

In the X-ray CT apparatus according to the twelfth aspect, the parameters other than the X-ray tube current values can be adjusted with the priorities assigned thereto. It is therefore possible to avoid a reduction in noise index value due to the restriction of the X-ray tube current values and adapt to a wider range of noise index values.

There is provided an X-ray CT apparatus according to a thirteenth aspect, wherein in the X-ray CT apparatus described in any of the first to twelfth aspects, said imaging or scanning condition setting device further includes device for setting the X-ray tube current or other parameter to the desired value having considered the size of the plane of the tomographic image.

In the X-ray CT apparatus according to the thirteenth aspect, a tomographic image maintained in image quality in the z-direction is obtained because the X-ray tube current or other parameter can be set to the desired value having considered the size of the plane of the tomographic image.

There is provided an X-ray CT apparatus according to a fourteenth aspect, wherein the imaging or scanning condition setting device further includes device for setting the X-ray tube current or other parameter to such a desired value that a standard deviation in the vicinity of a center at the tomographic image plane or the vicinity of a region of interest becomes constant.

In the X-ray CT apparatus according to the fourteenth aspect, each X-ray tube current value or other parameter can be set to such a desired value that the standard deviation in the vicinity of the center at the tomographic image plane or the vicinity of the region of interest becomes constant. Therefore, a tomographic image kept in image quality in the z-direction is obtained.

There is provided an X-ray CT apparatus according to a fifteenth aspect, wherein scanning of the X-rays is a variable-pitch helical scan or a helical shuttle scan.

In the X-ray CT apparatus according to the fifteenth aspect, a tomographic image kept in image quality in the z-direction is obtained at the variable-pitch helical scan or the helical shuttle scan.

There is provided an X-ray CT apparatus according to a sixteenth aspect, wherein in the X-ray CT apparatus described in any of the first to fifteenth aspects, scanning of the X-rays includes a range in which the scan is stopped in the body-axis direction of the subject.

In the X-ray CT apparatus according to the sixteenth aspect, the image quality can be controlled to be kept constant in the z-direction even though the range in which the scan is stopped exists. It is therefore possible to obtain a tomographic image kept in image quality in the z-direction.

There is provided an X-ray CT apparatus according to a seventeenth aspect, wherein in the X-ray CT apparatus described in any of the first to sixteenth aspects, further including display device for displaying a change in parameter value in the body-axis direction of the subject.

In the X-ray CT apparatus according to the seventeenth aspect, a change in parameter changed in the z-direction can be confirmed by a change in graph or numerical value. It can be confirmed whether the optimum parameter control is being performed.

There is provided an X-ray CT apparatus according to an eighteenth aspect, wherein in the X-ray CT apparatus described in the seventeenth aspect, said desired value corresponding to the X-ray irradiation position is calculated on the basis of the result of scout scan for setting scan conditions, and wherein said display device display a change in parameter value in association with the image of the subject obtained by the scout scan.

In the X-ray CT apparatus according to the eighteenth aspect, whether the optimum parameter control is being performed can be confirmed by graph-displaying and confirming a change in parameter in association with a scout image.

There is provided an X-ray CT apparatus according to a nineteenth aspect, wherein said image reconstructing device includes device for three-dimensionally image-reconstructing data detected by the X-ray detector.

In the X-ray CT apparatus according to the nineteenth aspect, a tomographic image which does not depend on spacing at each coordinate position in a body-axis direction of a subject, of a helical pitch or the like less reduced in archfact and is kept in image quality in the z-direction, can be obtained by executing the three-dimensional image reconstructing process.

There is provided an X-ray CT apparatus according to a twentieth aspect, wherein in the X-ray CT apparatus described in the nineteenth aspect, said image reconstructing device includes device for three-dimensionally image-reconstructing data obtained by one or more rotations where a helical pitch is 1 or less.

In the X-ray CT apparatus according to the twentieth aspect, when the helical pitch is 1 or less, a tomographic image good in image quality is obtained by using the data obtained by the rotations greater than one rotation.

According to the X-ray CT apparatus of the present invention, the image quality of each tomographic image that always satisfies the optimum noise standard value can be realized at an X-ray CT automatic exposure function without depending on an upper limit value of an output value of a tube current of an X-ray tube even though the output value is limited.

According to the X-ray CT apparatus of the present invention as well, priorities are assigned to plural parameters influencing each image and the plural parameters influencing the image are adjusted in order based on the priorities, thereby making it possible to efficiently realize the optimum image quality at an X-ray CT automatic exposure function as another effect.

That is, according to the present invention, an X-ray CT apparatus can be provided which is capable of improving image quality.

BRIEF DESCRIPTION OF THE DRAWINGS

FIG. 20 is a diagram showing an example 1 of a relationship between a helical pitch, the number of rotations for used data and X-ray tube currents at a variable-pitch helical scan or a helical shuttle scan.

DETAILED DESCRIPTION OF THE INVENTION

The present invention will hereinafter be explained in further detail by embodiments illustrated in the figures. Incidentally, the present invention is not limited to or by the embodiments.

First Embodiment

[Apparatus Configuration]

Figure 1:
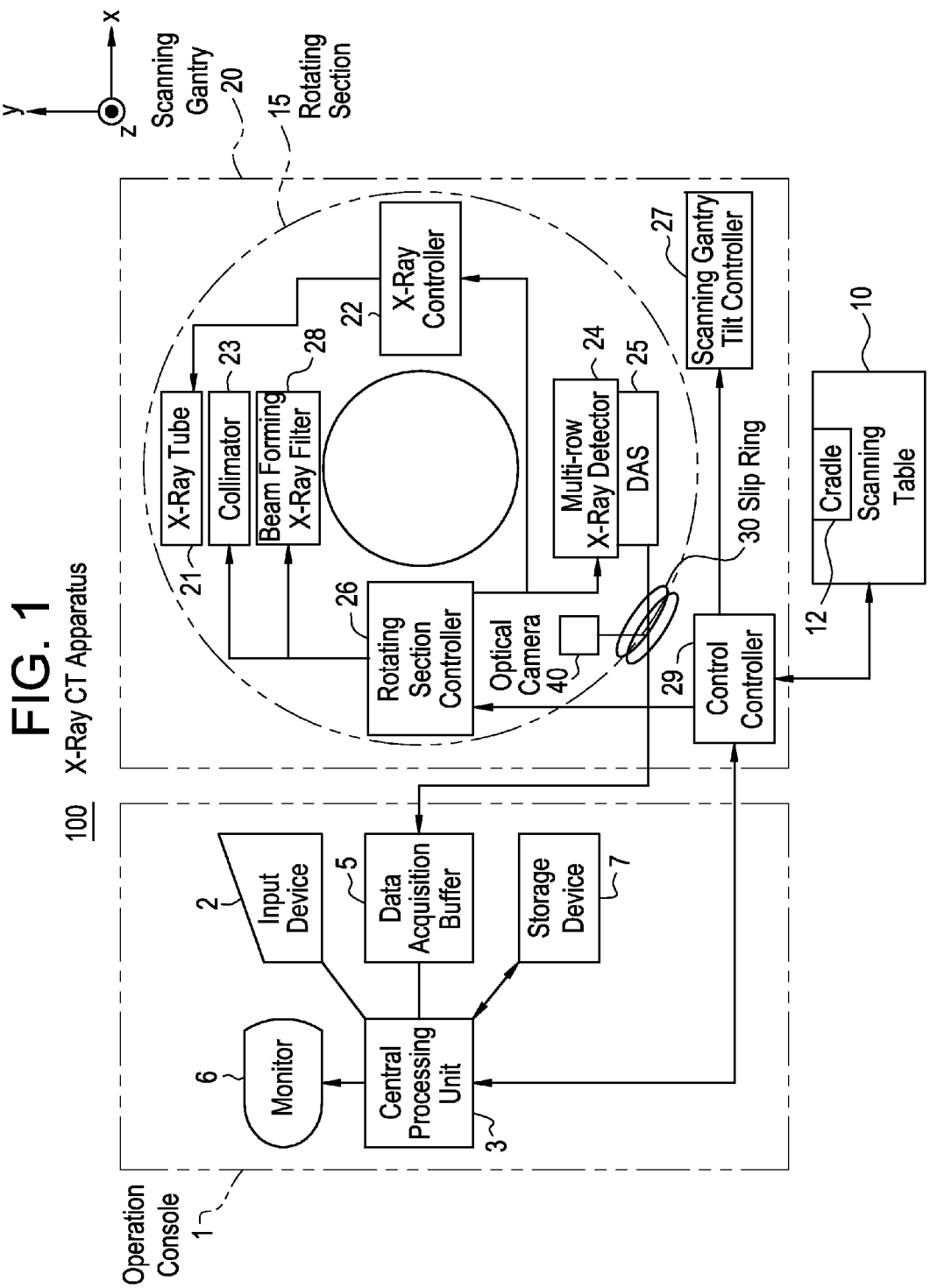
FIG. 1 is a block diagram showing an X-ray CT apparatus according to a first embodiment of the present invention.

A configuration block diagram of an X-ray CT apparatus according to a first embodiment of the present invention is illustrated as shown in FIG. 1.

As shown in FIG. 1, the X-ray CT apparatus 100 according to the present embodiment is equipped with an operation console 1, an imaging or scanning table 10 and a scanning gantry 20.

Figure 14:
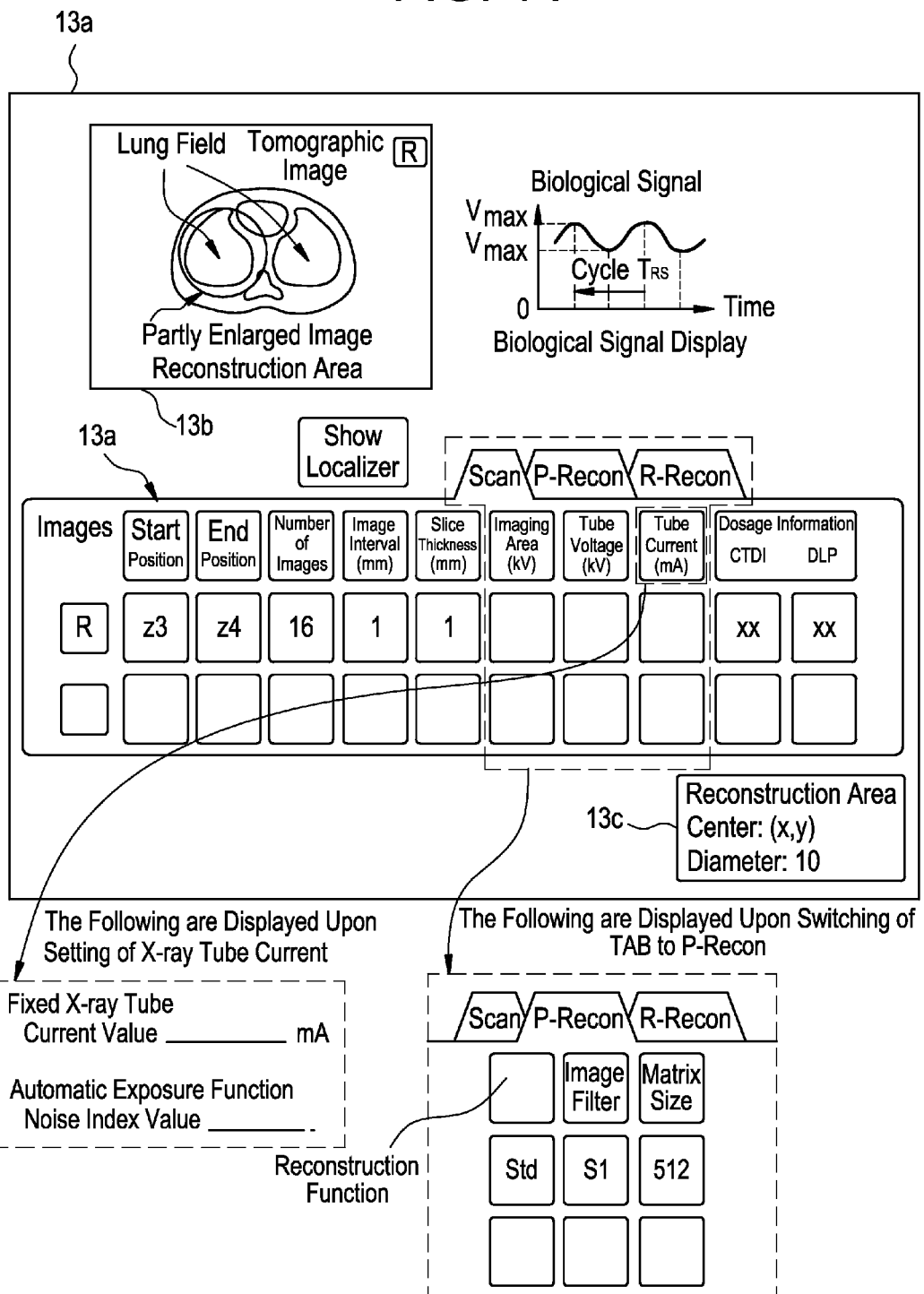
FIG. 14 is a diagram showing an imaging or scanning condition input screen of the X-ray CT apparatus.

As shown in FIG. 1, the operation console 1 includes an input device 2 which receives an input from an operator, a central processing unit 3 which executes data processing such as a pre-process, an image reconstructing process, a post-process, etc., a data acquisition buffer 5 which acquires or collects X-ray detector data acquired by the scanning gantry 20, a monitor 6 which displays a tomographic image image-reconstructed from projection data obtained by pre-processing the X-ray detector data, and a memory or storage device 7 which stores programs, X-ray detector data, projection data and X-ray tomographic images therein. In the present embodiment, imaging or photographing conditions are inputted from the input device 2 and stored in the storage device 7. An example of an imaging or scanning condition input screen is shown in FIG. 14.

As shown in FIG. 1, the scanning table 10 includes a cradle 12 which inserts and draws a subject into and from a bore or aperture of the scanning gantry 20 with the subject placed thereon. The cradle 12 is elevated and moved linearly on the scanning table 10 by a motor built in the scanning table 10.

Figure 2:
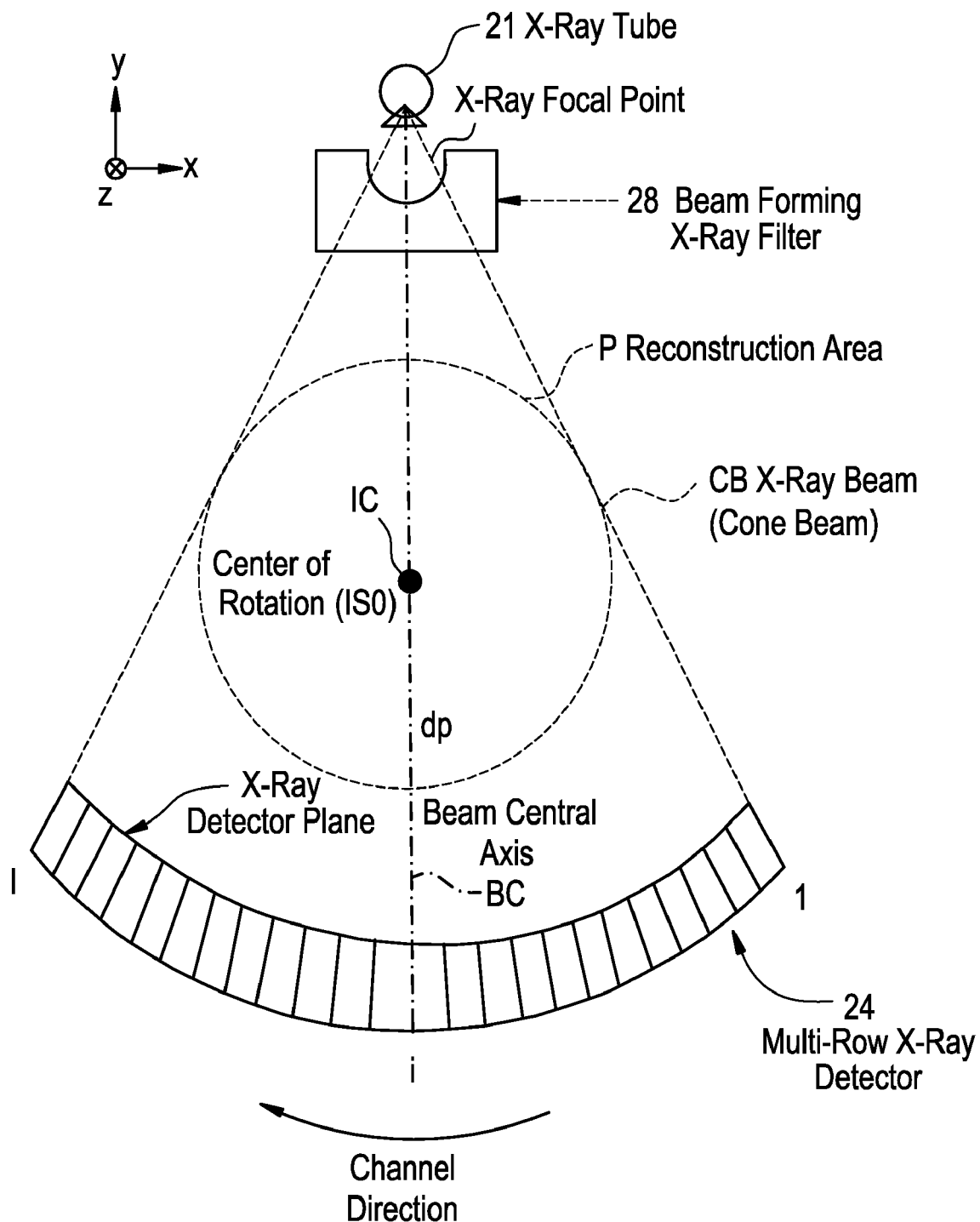
FIG. 2 is an explanatory diagram showing an X-ray generator (X-ray tube) and a multi-row X-ray detector as viewed in an xy plane.

As shown in FIG. 1, the scanning gantry 20 includes an X-ray tube 21, an X-ray controller 22, a collimator 23, a beam forming X-ray filter 28, a multi-row X-ray detector 24, a DAS (Data Acquisition System) 25, a rotating section controller 26 which controls the X-ray tube 21 or the like so as to be rotated about a body axis of the subject, and a control controller 29 which swaps control signals or the like with the operation console 1 and the scanning table 10. Here, the beam forming X-ray filter 28 is of an X-ray filter configured so as to be thinnest in thickness as viewed in the direction of X-rays directed to the center of rotation corresponding to the center of imaging, to increase in thickness toward its peripheral portion and to be able to further absorb the X-rays as shown in FIG. 2. Therefore, in the present embodiment, the body surface of a subject whose sectional shape is nearly circular or elliptic can be less exposed to radiation. The scanning gantry 20 can be tiled about ±30° or so forward and rearward as viewed in the z-direction by a scanning gantry tilt controller 27.

The X-ray tube 21 and the multi-row X-ray detector 24 are rotated about the center of rotation IC as shown in FIG. 2. Assuming that the vertical direction is a y direction, the horizontal direction is an x direction and the travel direction of the table and cradle orthogonal to these is a z-direction, the plane at which the X-ray tube 21 and the multi-row X-ray detector 24 are rotated, is an xy plane. The direction in which the cradle 12 is moved, corresponds to the z-direction.

Figure 3:
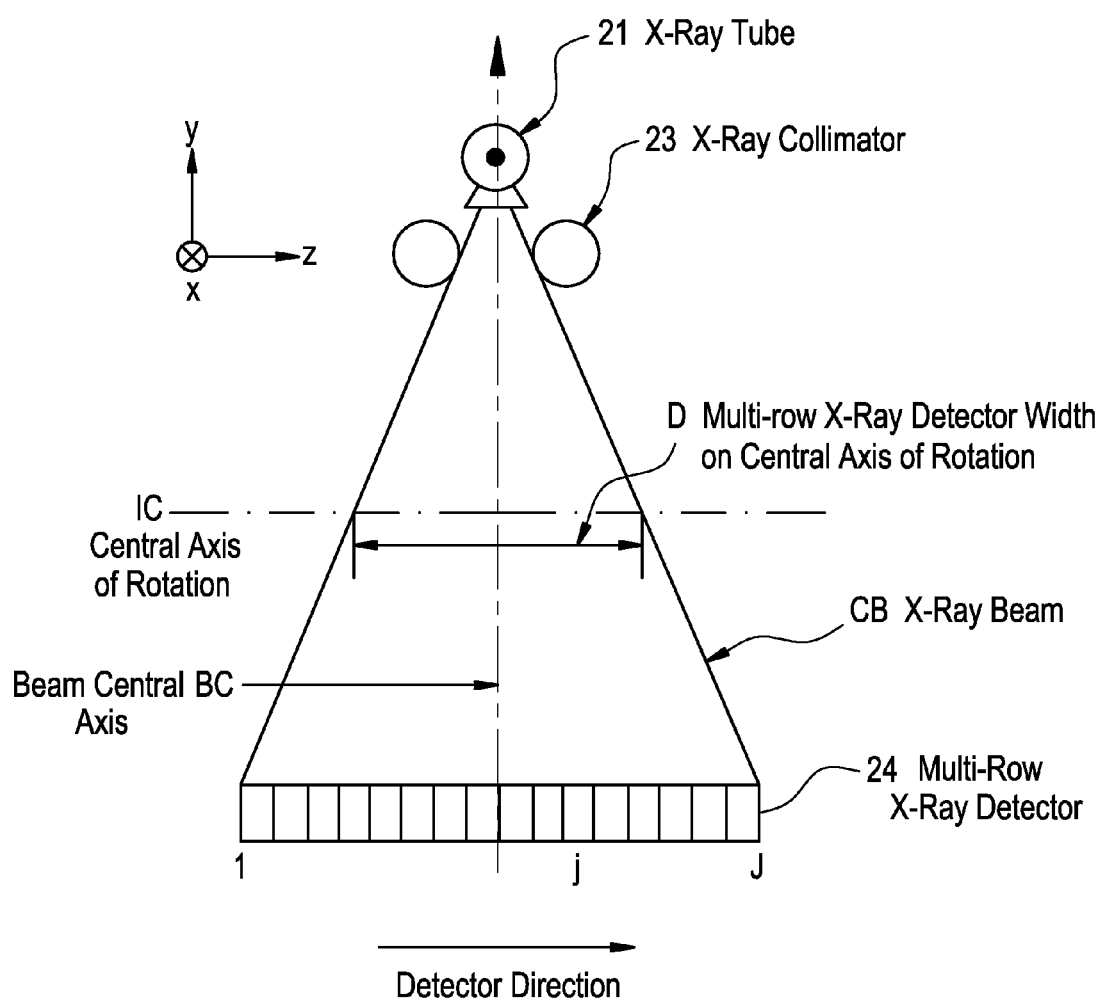
FIG. 3 is an explanatory diagram illustrating the X-ray generator (X-ray tube) and the multi-row X-ray detector as viewed in a yz plane.

FIGS. 2 and 3 are explanatory diagrams showing a geometrical arrangement or layout of the X-ray tube 21 and the multi-row X-ray detector 24 as viewed from the xy plane or yz plane.

As shown in FIG. 2, the X-ray tube 21 generates an X-ray beam called a cone beam CB. Incidentally, when the direction of a central axis of the cone beam CB is parallel to the y direction, this is defined as a view angle 0°. The multi-row X-ray detector 24 has X-ray detector rows corresponding to, for example, 256 rows as viewed in the z-direction. Each of the X-ray detector rows has X-ray detector channels corresponding to, for example, 1024 channels as viewed in a channel direction.

As shown in FIG. 2, the X-ray beam emitted from an X-ray focal point of the X-ray tube 21 is spatially controlled in X-ray dosage by the beam forming X-ray filter 28 in such a manner that more X-rays are radiated in the center of a reconstruction area or plane P and less X-rays are radiated at a peripheral portion of the reconstruction area P. Thereafter, the X-rays are absorbed by the subject that exists inside the reconstruction area P, and the X-rays transmitted through the subject are acquired by the multi-row X-ray detector 24 as X-ray detector data.

As shown in FIG. 3, the X-ray beam emitted from the X-ray focal point of the X-ray tube 21 is controlled in the direction of a slice thickness of a tomographic image by the collimator 23. That is, the X-ray beam is controlled in such a manner that the width of the X-ray beam becomes D at a central axis of rotation IC. Then, the X-rays are absorbed into the subject existing in the vicinity of the central axis of rotation IC, and the X-rays transmitted through the subject are acquired by the multi-row X-ray detector 24 as X-ray detector data.

Thus, the projection data acquired by application of the X-rays are outputted from the multi-row X-ray detector 24 to the DAS 25 and A/D converted by the DAS 25. Then, the data are inputted to the data acquisition buffer 5 via a slip ring 30. Thereafter, the data inputted to the data acquisition buffer 5 are processed by the central processing unit 3 in accordance with the corresponding program stored in the storage device 7, so that the data are image-reconstructed as a tomographic image. Afterwards, the tomographic image is displayed on a display screen of the monitor 6.

Incidentally, the X-ray tube 21 and the X-ray controller 22 always manage a loading dose of the X-ray tube corresponding to the history of each X-ray output outputted up to that time by software of the central processing unit 3 or software of the X-ray controller 22. Thus, the outputtable maximum X-ray output condition of the X-ray tube 21 change momentarily. The X-ray tube 21 is guarded and protected by such X-ray tube load management function in such a manner that the breakage of the X-ray tube 21 does not occur.

[Outline of Operations]

The outline of each operation of the X-ray CT apparatus 100 is shown below.

Figure 4:
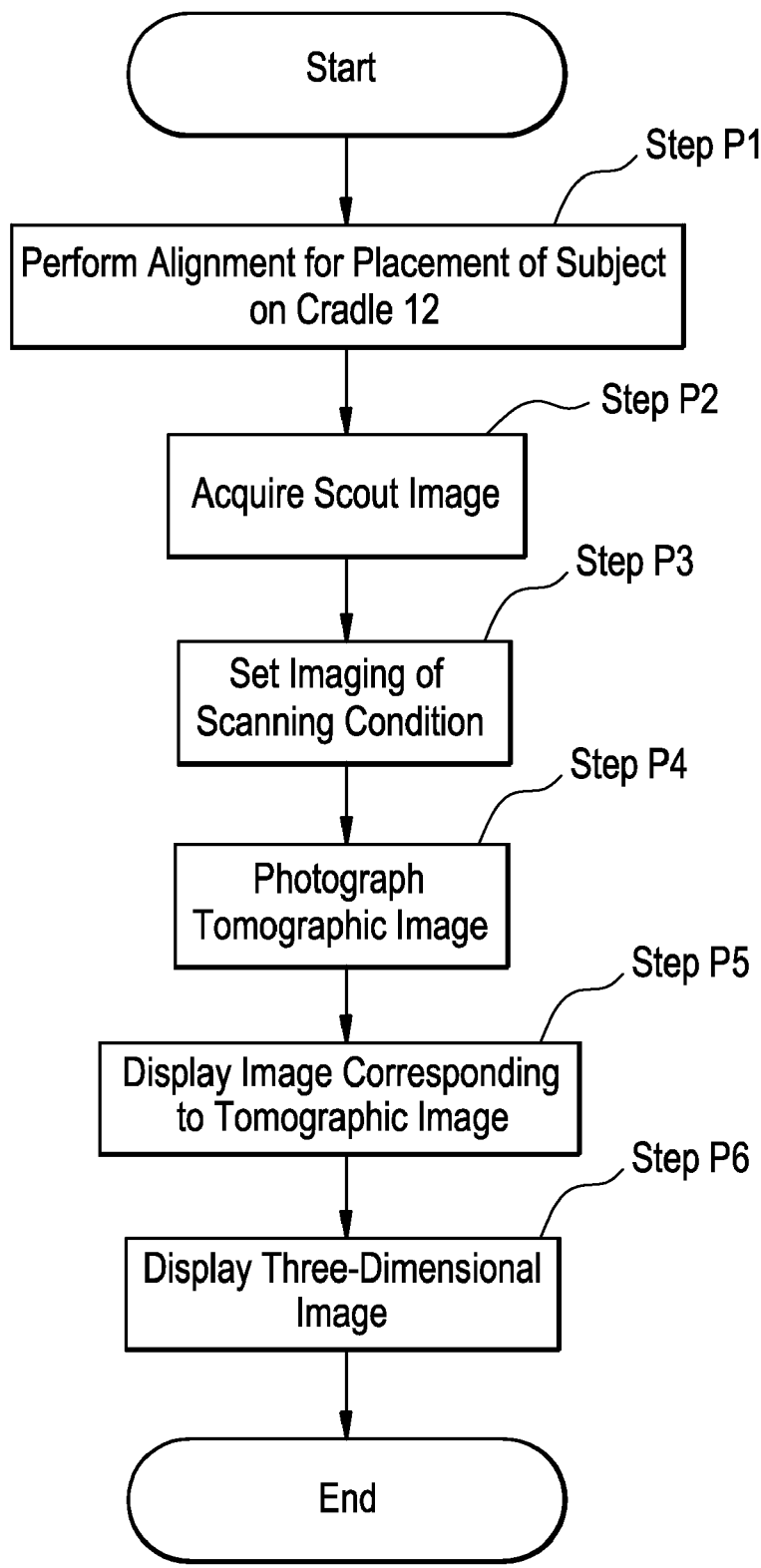
FIG. 4 is a flow chart depicting the flow of subject imaging.

FIG. 4 is a flow chart showing the outline of the operation of the X-ray CT apparatus according to the present embodiment.

At Step P1, the subject is first placed on the cradle 12 and its alignment is made.

Here, a slice light center position of the scanning gantry 20 is aligned with a reference point of each region of the subject placed on the cradle 12.

Next, at Step P2, scout image acquisition is performed as shown in FIG. 4.

Here, a scout image is normally photographed at view angles of 0° and 90°. Incidentally, only a 90° scout image may be photographed or imaged as in the case of, for example, the head, depending upon each region. The details of the photographing of the scout image will be described later.

Next, at Step P3, an imaging or photographing condition is set as shown in FIG. 4.

Here, the imaging or scanning condition is normally set while the position and size of a tomographic image to be photographed are being displayed on a scout image. In this case, the whole X-ray dosage information corresponding to one helical scan, variable-pitch helical scan, helical shuttle scan, conventional scan (axial scan) or cine scan is displayed.

When the number of rotations of an X-ray data acquisition system of a rotating section lying in the scanning gantry 20 or the set value of imaging time is inputted to a user interface displayed on such a monitor 6 as shown in FIG. 14, X-ray dosage information corresponding to the inputted number of rotations in the area of interest of the subject or the time inputted is displayed at the user interface displayed on such a monitor 6 as shown in FIG. 14.

Incidentally, in the present embodiment, the imaging or scanning condition is set using a so-called automatic exposure function. The setting of the imaging or scanning condition by the automatic exposure function will be described later.

Next, at Step P4, tomographic image photography is performed as shown in FIG. 4.

The details of the tomographic image photography and the image reconstruction will be described in detail later.

Next, at Step P5, an image-reconstructed tomographic image is displayed as shown in FIG. 4.

Next, at Step P6, a three-dimensional image display is performed as shown in FIG. 4.

Figure 15:
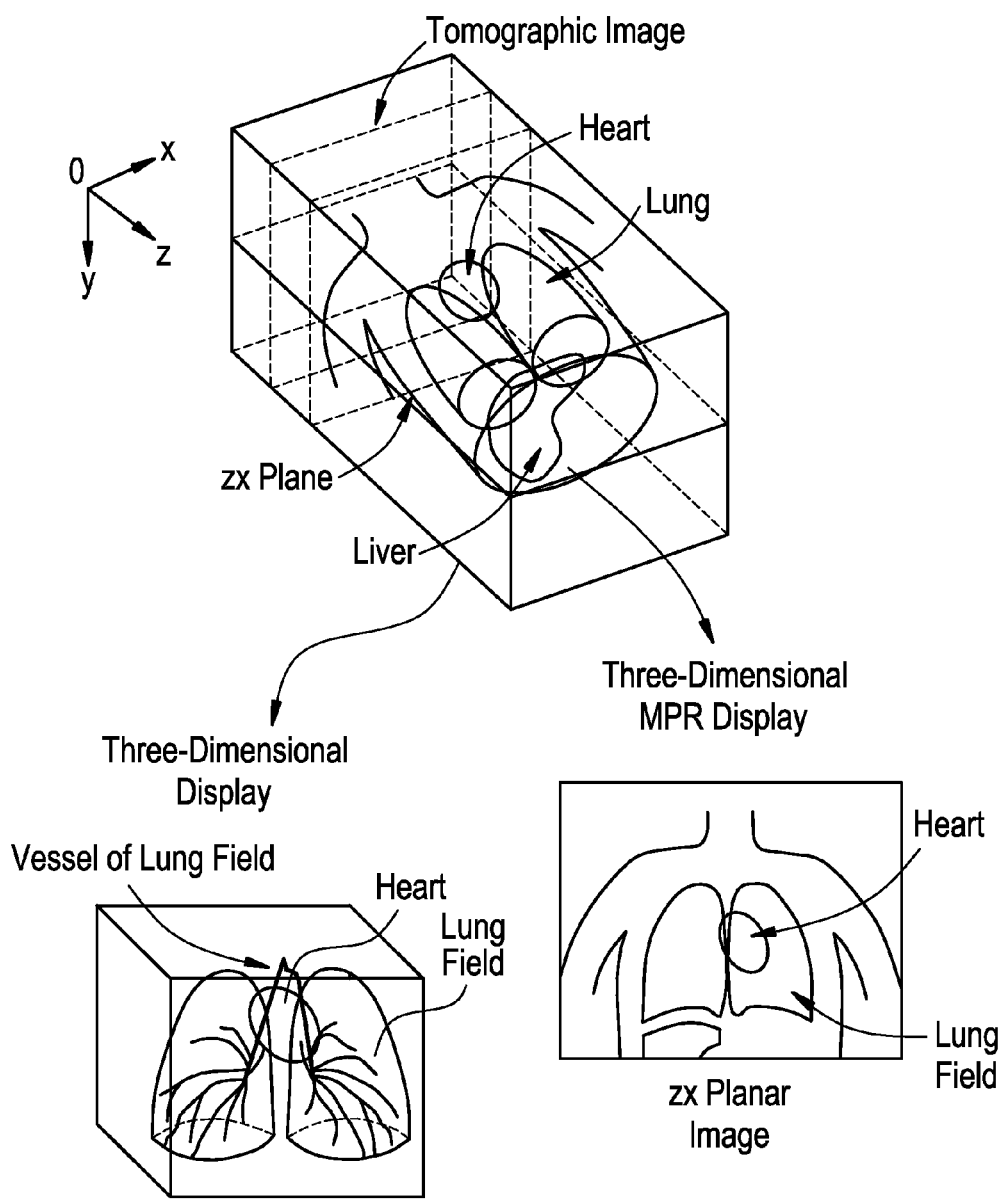
FIG. 15 is a diagram showing an example illustrative of a three-dimensional MPR display and a three-dimensional display.

Here, a tomographic image photographed continuously in a z-direction is defined as a three-dimensional image and three-dimensionally image-displayed as shown in FIG. 15.

As methods for the three-dimensional image display, may be mentioned, as shown in FIG. 15, a volume rendering three-dimensional image display method, an MIP (Maximum Intensity Projection) image display method, an MPR (Multi Plain Reformat) image display method, a three-dimensional reprojection image display method, etc. They are used and made available properly according to diagnostic applications.

[Setting of Imaging or Scanning Condition by Automatic Exposure Function]

The operation at the time that the X-ray CT apparatus sets the imaging or scanning condition by the automatic exposure function at Step P3 referred to above, will be explained.

When the automatic exposure function is used upon the imaging or scanning condition setting at Step P3, the central processing unit 3 calculates profile areas (sectional areas) at respective z-direction coordinate positions for obtaining X-ray projection data at the subject upon imaging on the basis of the scout image about the 0° direction (y-axis direction) or 90° direction (x-axis direction), which has been obtained at Step P2 referred to above. Then, the optimum X-ray tube current value at each z-direction coordinate position is set as the imaging or scanning condition, based on each of the calculated profile areas. The monitor 6 displays an image indicative of the set imaging or scanning condition. A z-direction change in parameter of the X-ray automatic exposure function is displayed so as to correspond to the scout image by using at least one method using a graph or numerical values.

Figure 16A:
FIG. 16(a) shows a constant X-ray tube current.
Figure 16B:
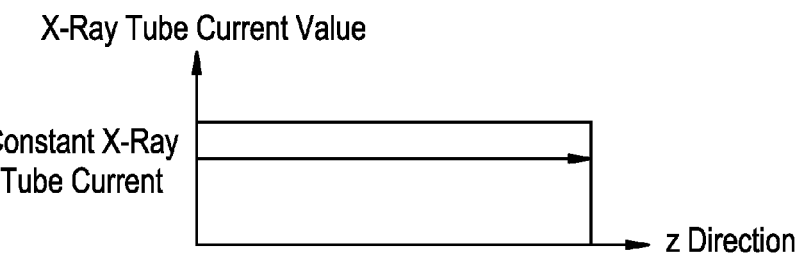
FIG. 16(b) shows a change of an X-ray tube current in an xy plane.
Figure 16C:
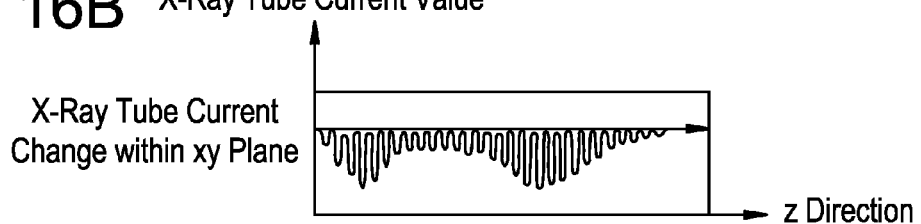
FIG. 16(c) shows a change of an X-ray tube current in a z-direction.
Figure 16D:
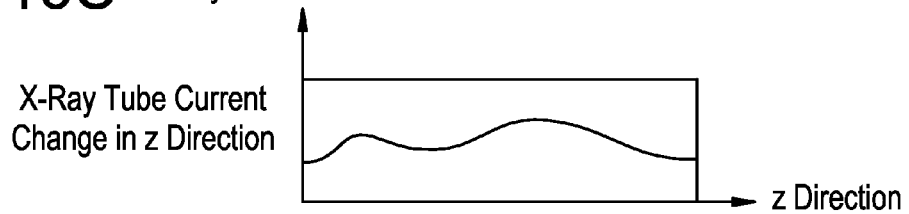
FIG. 16(d) shows a change of an xyz three-dimensional X-ray tube current.
Figure 17A:
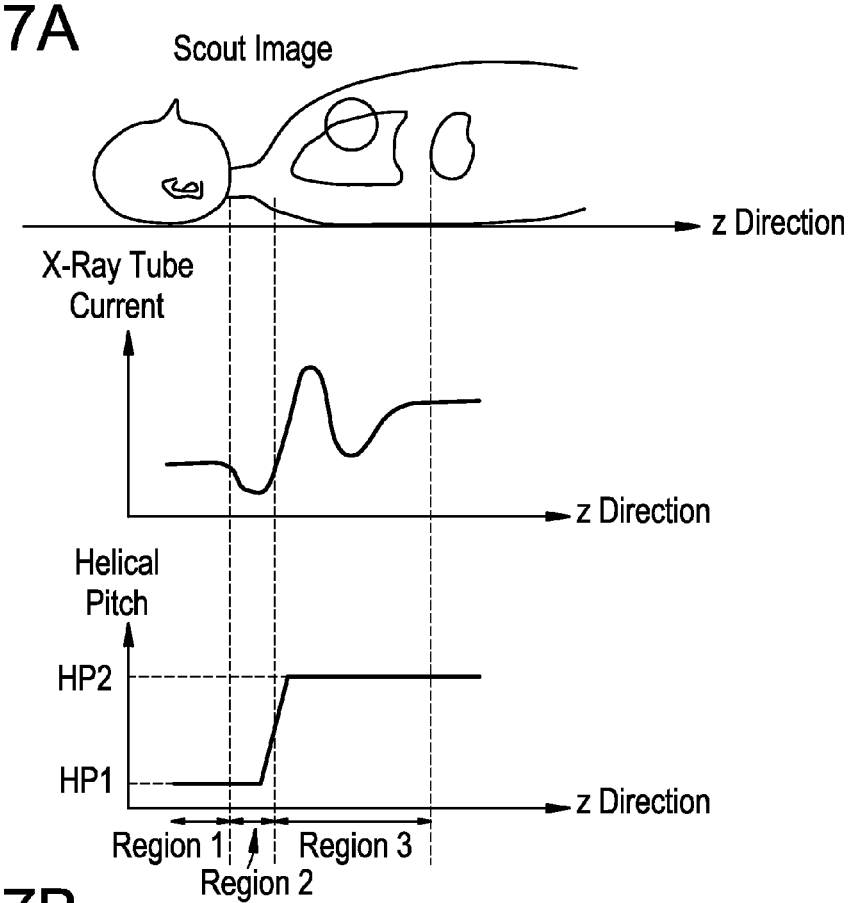
FIG. 17(a) shows where an X-ray tube current of the X-ray tube is not limited.

FIG. 17(a) illustrates X-ray tube current values and helical pitches set where the thermal capacity of the X-ray tube is sufficiently large and no limitation is placed on the tube current of the X-ray tube. Here, as shown in FIG. 17(a), a plan is made so as to photograph or image, for example, regions 1 and 2 of a subject on condition that the helical pitch HP is set to 1 and to photograph a region 3 of the subject on condition that the helical pitch HP is set to 2. Then, the optimum X-ray tube current is determined at each z-direction coordinate position of the subject, based on the scout image as viewed in the 90° direction. In this case, the set value of the X-ray tube current is decided so as to correspond to a change in the profile area as viewed in the z-direction, of the subject as shown in FIG. 16(c) as mentioned above. In addition to the above, the set value of the X-ray tube current may be determined so as to correspond to a change in X-ray penetration path within the xy plane of the subject as shown in FIG. 16(b) as described above. Thus, when the thermal capacity of the X-ray tube is sufficiently large and no limitation is placed on the tube current of the X-ray tube, the optimum imaging or scanning condition is adequately obtained by adjusting the setting of the X-ray tube current.

Figure 17B:
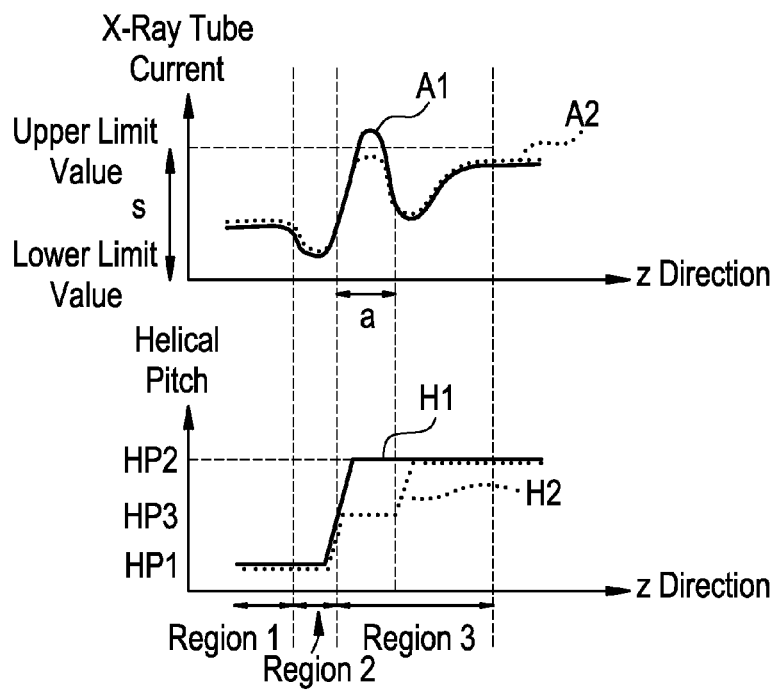
FIG. 17(b) shows a change of each helical pitch where an X-ray tube current of the X-ray tube is limited.

When, however, the thermal capacity of the X-ray tube is not large sufficiently and the X-ray tube current is limited as shown in FIG. 17(b), a plan is made so as to scan the regions 1 and 2 of the subject with the helical pitch HP as 1 and photograph the region 3 with the helical pitch HP2 as 2. When the optimum X-ray tube current at each z-direction coordinate position is determined based on the scout image as viewed in the 90° direction, it might exceed an upper limit value of a settable X-ray tube current as described above.

In such a case, scanning is done up to now at the upper limit value of the X-ray tube current. Therefore, there was a case in which an image lying within a range a set beyond the upper limit value of the X-ray tube current as viewed in the z-direction was reduced in image quality. Thus, in the embodiment according to the present invention, deterioration in image quality is prevented by changing a parameter for other imaging or scanning condition related to the image quality in such a case. A location at which the helical pitch HP is set to 2 as indicated by a solid line in FIG. 17(b) is changed to a helical pitch HP3 within the range a as indicated by a broken line in FIG. 17(b). This prevents deterioration in image quality in the present embodiment.

Assuming that the helical pitch is set to (HP3/HP2) times as described above, the amount of X-ray tube current at a unit z-direction width per unit time having considered the helical pitch becomes approximately equivalent to the setting of the X-ray tube current to (HP2/HP3) times at X-ray tube current conversion in terms of image quality for image noise. Therefore, if the helical pitch HP is changed to 3 with respect to only the portion of the range a as shown in FIG. 17(b), equivalent image quality can be obtained even though the X-ray tube current supplied to the X-ray tube 21 is relatively low. By lowering the helical pitch to HP3 with respect to the determined X-ray tube current, the X-ray tube current to be determined can be reduced to (HP3/HP2) times in FIG. 17(b). Thus, even when the X-ray tube current is scanned as a settable range, the image quality of the optimum image noise can be obtained. When the helical pitch is not reduced, an improvement in image noise can be carried out by a projection data spatial channel-direction filter ring or the like corresponding to other image noise improving device.

[Flow of Processing for Setting of Imaging or Scanning Condition by Automatic Exposure Function]

A flow of processing for setting an imaging or scanning condition by an automatic exposure function will be explained below.

Figure 18:
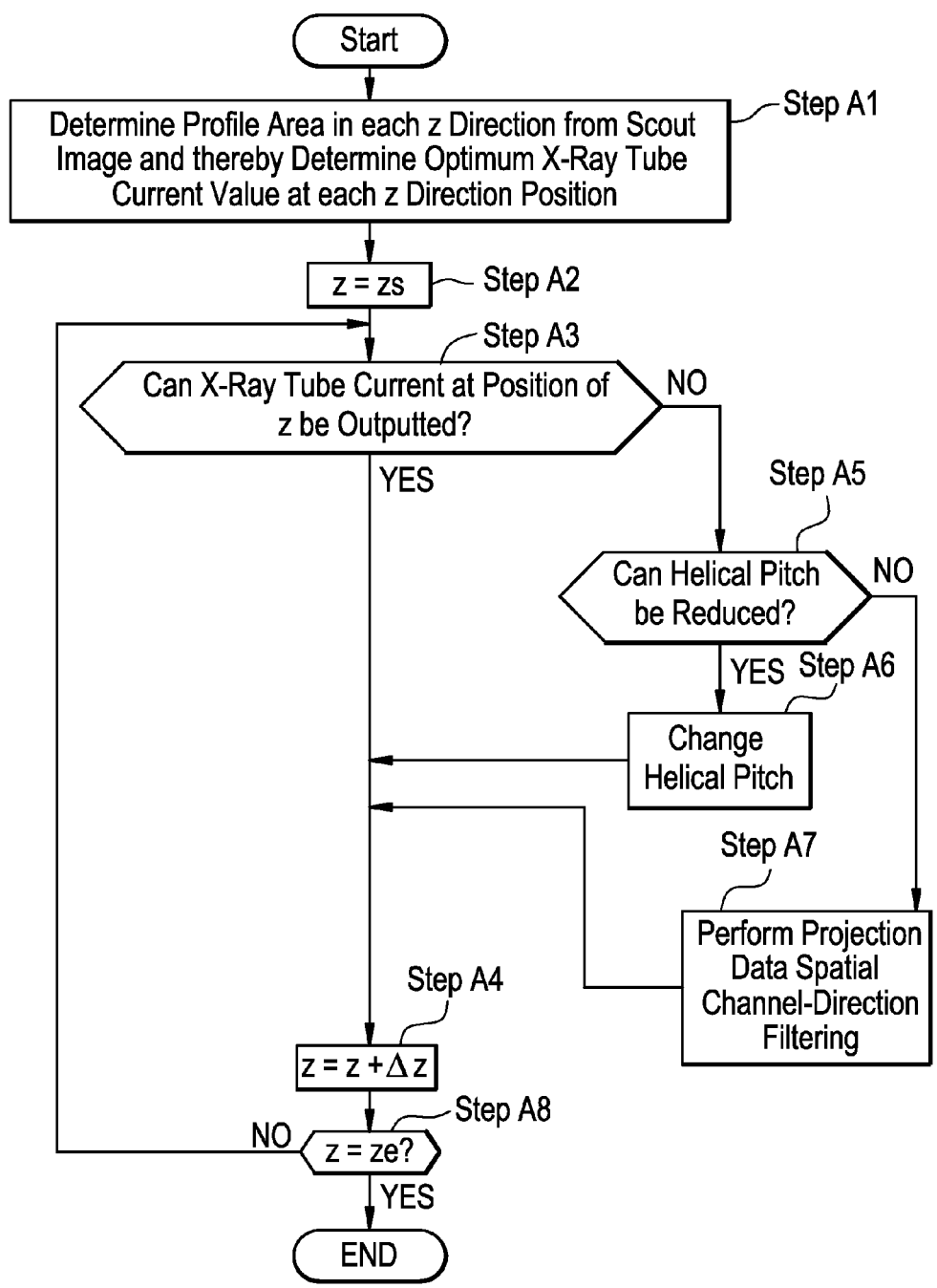
FIG. 18 is a flowchart showing an X-ray automatic exposure function for making up an X-ray tube current shortage by a helical pitch or a projection data spatial channel-direction filter.

FIG. 18 is a flowchart showing a flow of processing for setting of an imaging or scanning condition by an automatic exposure function. An X-ray automatic exposure function for making up for an X-ray current shortage using a helical pitch or a projection data spatial channel direction filter will be explained here.

At Step A1, a profile area in each z-direction is determined from a scout image as shown in FIG. 18 to obtain the optimum X-ray tube current value at each z-direction position.

Next, at Step A2, z=zs as shown in FIG. 18.

Here, a z-direction start coordinate is defined as zs. That is, at the present or actual Step, the central processing unit 3 executes data processing in such a manner that each z-direction coordinate position is set to an initial value to control an imaging or scanning condition at each z-direction coordinate position below.

Next, at Step A3, it is determined as shown in FIG. 18 whether an X-ray tube current at the position of z can be outputted. If it is determined that the output thereof can be performed (if the answer is found to be YES), then the processing flow proceeds to Step A4. If it is determined that the output thereof cannot be carried out (if the answer is found to be NO), then the processing flow proceeds to Step A5.

Here, the central processing unit 3 determines that when an X-ray tube current lying within the range of outputtable X-ray tube currents at respective times, of the X-ray tube is requested, the set value of the X-ray tube current can be outputted from the central processing unit 3 to the X-ray controller 22 via the control controller 29.

On the other hand, when an X-ray tube current lying outside the range of the outputtable X-ray tube currents at the respective times, of the X-ray tube is requested, the central processing unit 3 determines that the set value of the X-ray tube current cannot be outputted from the central processing unit 3 to the X-ray controller 22 via the control controller 29.

At Step A4, $z=z+\Delta z$ as shown in FIG. 18.

That is, here, the central processing unit 3 executes data processing in such a manner that the z-direction coordinate position is set to the following z-direction coordinate position.

At Step A5, it is determined as shown in FIG. 18 whether the helical pitch can be reduced or lowered. If it is determined that the helical pitch can be reduced (if the answer is found to be YES), then the processing flow proceeds to Step A6. If it is determined that the helical pitch cannot be reduced (if the answer is found to be NO), then the processing flow proceeds to Step A7.

Described specifically, the central processing unit 3 determines that when the z-direction travel speed of the cradle 12 of the scanning table 10 falls within a controllable range, the helical pitch can be reduced.

On the other hand, when the z-direction travel speed of the cradle of the scanning table 10 falls within an uncontrollable range, the central processing unit 3 determines that the helical pitch cannot be reduced.

At Step A8, the helical pitch is changed as shown in FIG. 18.

Here, the central processing unit 3 changes and sets the initially-set helical pitch to another helical pitch corresponding to the minimum speed, based on the range in which the z-direction travel speed of the cradle 12 of the scanning table 10 can be controlled.

At Step A7, projection data spatial channel-direction filtering is performed as shown in FIG. 18.

Here, the central processing unit 3 effects the projection data spatial channel-direction filtering on pre-processed X-ray projection data or X-ray projection data subjected to a beam hardening correction. Incidentally, here, the terms "projection data spatial channel-direction filtering" is specifically called channel-direction space filtering processing convolved on X-ray projection data of respective rows.

At Step A8, it is determined as shown in FIG. 18 whether $z \geq ze$. If $z \geq ze$ (if the answer is found to be YES), then the processing is terminated. If $z \geq ze$ is not satisfied (if the answer is found to be NO), then the processing flow returns to Step A3. However, a z-direction end coordinate is defined as ze.

According to the above processing flow, the parameter of each X-ray tube current corresponding to the parameter of the image noise is given priority. Next, the helical pitch corresponding to the parameter of the image noise at each helical scan is given priority. Then, the projection data spatial channel-direction filtering corresponding to the parameter of the image noise is given priority, whereby the optimum image noise can be realized. That is, priorities are assigned to the parameters of the plural pieces of image noise to control the same, whereby the optimum image noise is realized. An advantageous effect is brought about in that the image quality can further be optimized by setting the priorities between the plural parameters in this way and sequentially setting the parameters, based on the priorities

[Outline of Operations at Tomographic Image Photography and Scout Image Photography]

The outline of operations at the execution of tomographic image photography (Step P4 in FIG. 4) and scout image photography (Step P2 in FIG. 4) will be shown below.

Figure 5:
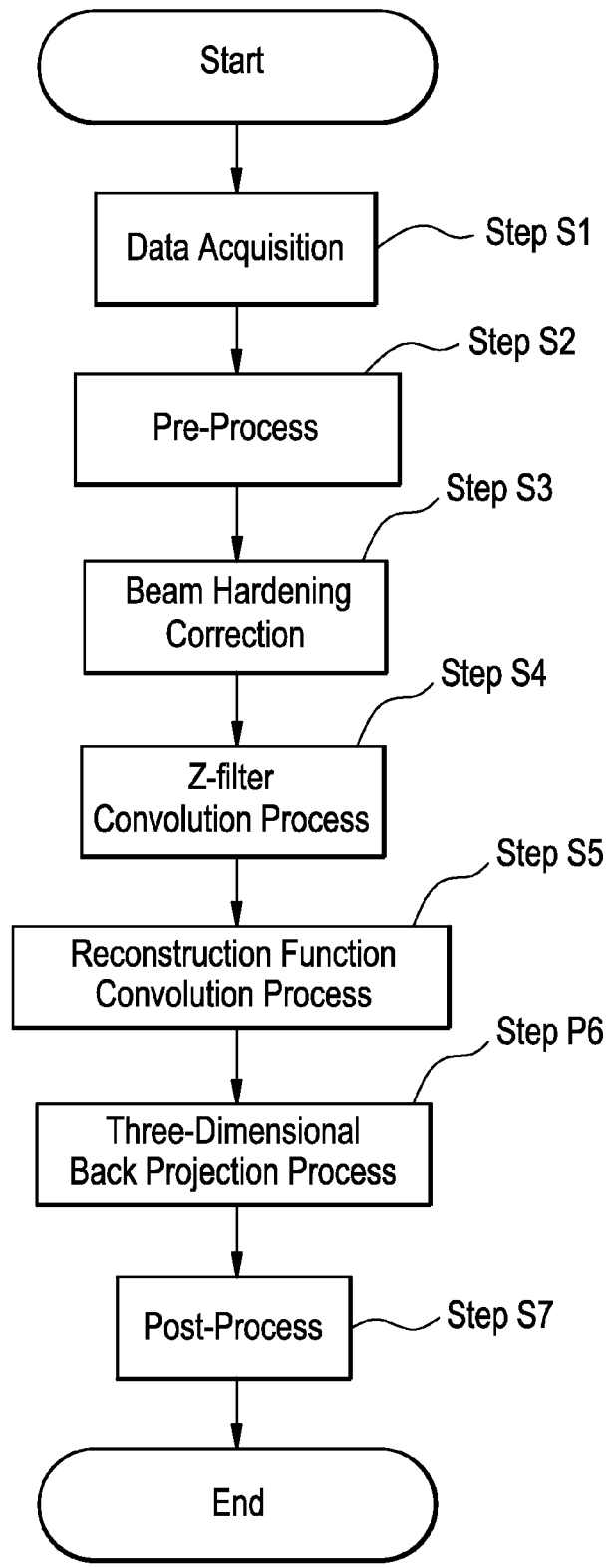
FIG. 5 is a flow chart showing a schematic operation for image reconstruction, of the X-ray CT apparatus according to the first embodiment of the present invention.

FIG. 5 is a flow chart showing the outline of the operations for the tomographic image photography and scout image photography, of the X-ray CT apparatus 100 of the embodiment according to the present invention.

At Step S1, data acquisition is first performed as shown in FIG. 5.

Here, when the data acquisition is carried out by a helical scan, the operation of rotating the X-ray tube 21 and the multi-row X-ray detector 24 about the subject and carrying out data acquisition of X-ray detector data while the cradle 12 placed on the scanning table 10 is being linearly moved, is performed. Then, a table linear movement z-direction coordinate position Ztable(view) is added to X-ray detector data D0 (view, j, i) indicated by a view angle view, a detector row number j and a channel number i. Upon the helical scan for acquiring or collecting the X-ray detector data in this way, data acquisition in a constant-speed range is performed.

When data acquisition is performed by a variable-pitch helical scan or a helical shuttle scan, the data acquisition is performed even at acceleration and deceleration in addition to the data acquisition in the constant-speed range.

The z-direction coordinate position may be added to X-ray projection data or may be associated with X-ray projection data as another file. When the X-ray projection data is three-dimensionally image-reconstructed upon the variable-pitch helical scan, information about the z-direction coordinate position is used. By using it upon the helical scan, conventional scan (axial scan) or cine scan, an improvement in the accuracy of each image-reconstructed tomographic image and an improvement in its image quality can be realized.

Position control data for the cradle 12 of the scanning table 10 may be used for the z-direction coordinate position. Alternatively, a z-direction coordinate position at each time, which is predicted from an imaging operation set upon the setting of the imaging or scanning condition, can also be used therefor.

When the data acquisition is performed by the conventional scan (axial scan) or the cine scan, the data acquisition system is rotated once or plural times while the cradle 12 placed on the scanning table 10 is being fixed to a given z-direction position, thereby to perform data acquisition of X-ray detector data. The cradle 12 is moved to the next z-direction position as needed and thereafter the data acquisition system is rotated once or plural times again to perform data acquisition of X-ray detector data.

Upon the scout image photography, the operation of fixing the X-ray tube 21 and the multi-row X-ray detector 24 and performing data acquisition of X-ray detector data while the cradle 12 placed on the scanning table 10 is being linearly moved, is performed.

Next, at Step S2, a pre-process is performed as shown in FIG. 5.

Figure 6:
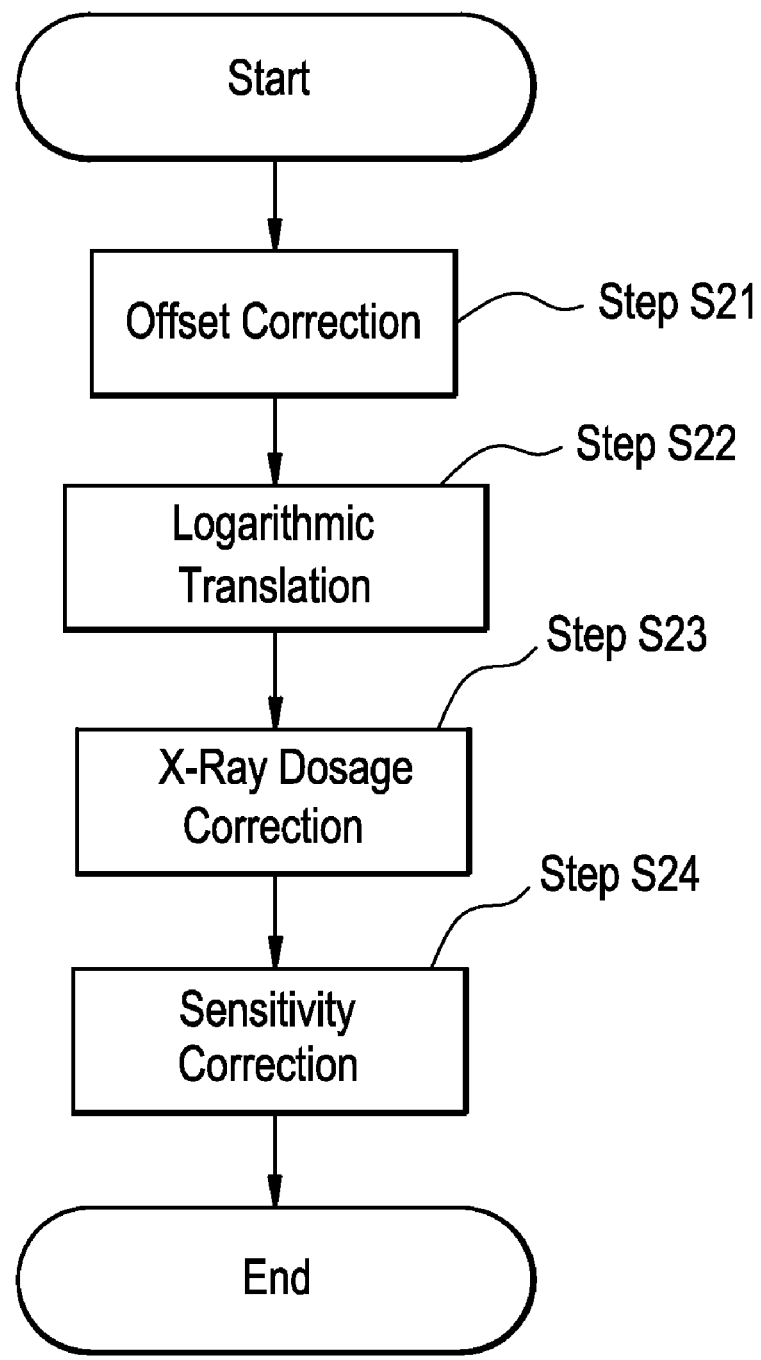
FIG. 6 is a flow chart illustrating the details of a pre-process.

Here, the pre-process is performed on the X-ray detector data D0 (view, j, i) to convert it into projection data. As shown in FIG. 6, the pre-process comprises an offset correction of Step S21, logarithmic translation of Step S22, an X-ray dosage correction of Step S23 and a sensitivity correction of Step S24.

If the pre-processed X-ray detector data is displayed upon the scout image photography with each of a pixel size in the channel direction and a pixel size in the z-direction corresponding to the cradle linear moving direction being made coincident with a display pixel size of the monitor 6, then the X-ray detector data is completed as the corresponding scout image.

Next, at Step S3, a beam hardening correction is performed as shown in FIG. 5.

Here, the beam hardening correction is effected on the pre-processed projection data D1 (view, j, i). Assuming that upon the beam hardening correction of Step S3, projection data subjected to the sensitivity correction S24 at the pre-process S2 is defined as D1 (view, j, i) and data subsequent to the beam hardening correction of Step S3 is defined as D11 (view, j, i), the beam hardening correction is expressed in the form of, for example, a polynomial as given by the following equation (1).

[Equation 1]

$$D11(\text{view},j,i) = D1(\text{view},j,i) \cdot (B_0(j,i) + B_1(j,i) \cdot D1(\text{view},j,i) + B_2(j,i) \cdot D1(\text{view},j,i)^2) \quad (1)$$

Since, at this time, the independent beam hardening corrections can be carried out for every j row of the detectors, the difference between X-ray energy characteristics for each row of the detector can be corrected if tube voltages of respective data acquisition systems are different on the imaging or scanning condition.

Next, at Step S4, a z-filter convolution process is performed as shown in FIG. 5.

Here, the z-filter convolution process for applying filters in the z-direction (row direction) is effected on the projection data D11 (view, j, i) subjected to the beam hardening correction.

That is, after the pre-process at each view angle and each data acquisition system, projection data of the multi-row X-ray detector D11 (view, j, i) (where i=1 to CH and j=1 to ROW) subjected to the beam hardening correction is multiplied in the row direction by filters in which such row-direction filter sizes as expressed in the following equations (2) and (3) are five rows, for example. However, (the equation 3) is satisfied.

[Equation 2]

$$(w_1(i), w_2(i), w_3(i), w_4(i), w_5(i)) \quad (2)$$

[Equation 3]

$$\sum_{k=1}^{5} w_k(i) = 1 \quad (3)$$

The corrected detector data D12 (view, j, i) is given as expressed in the following equation (4):

[Equation 4]

$$D12(\text{view}, j, i) = \sum_{k=1}^{5} (D11(\text{view}, j+k-3, i) \cdot w_k(j)) \quad (4)$$

Incidentally, assuming that the maximum value of the channel is CH and the maximum value of the row is ROW, the following equations (5) and (6) are established.

[Equation 5]

$$D11(\text{view},-1,i) = D11(\text{view},0,i) = D11(\text{view},1,i) \quad (5)$$

[Equation 6]

$$D11(\text{view},\text{ROW},i) = D11(\text{view},\text{ROW}+1,i) = D11(\text{view},\text{ROW}+2,i) \quad (6)$$

When row-direction filter coefficients are changed for every channel, slice thicknesses can be controlled depending upon the distance from an image reconstruction center. In a tomographic image, its peripheral portion generally becomes thicker in slice thickness than the reconstruction center thereof. Therefore, the row-direction filter coefficients are changed at the central and peripheral portions, and the row-direction filter coefficients are widely changed in width in the neighborhood of a central channel and narrowly changed in width in the neighborhood of a peripheral channel, thereby making it possible to make the slice thicknesses uniform at both the peripheral portion and the image reconstruction center.

Controlling the row-direction filter coefficients at the central and peripheral channels of the multi-row X-ray detector 24 in this way makes it possible to control the slice thicknesses at the central and peripheral portions. Thickening the slice thickness slightly by each row-direction filter yields extensive improvements in both artifact and noise. Thus, the degree of the improvement in artifact and the degree of the improvement in noise can also be controlled. That is, it is possible to control a three-dimensionally image-reconstructed tomographic image, i.e., image quality in the xy plane. In addition to above, a tomographic image having a thin slice thickness can also be realized by setting row-direction (z-direction) filter coefficients to deconvolution filters.

Next, at Step S5, a reconstruction function convolution process is performed as shown in FIG. 5.

That is, projection data D12 (view, j, i) subjected to the z-filter convolution process is subjected to Fourier transformation and multiplied by a reconstruction function, followed by being subjected to inverse Fourier transformation. Assuming that upon the reconstruction function convolution process S5, data subsequent to the z filter convolution process is defined as D12, data subsequent to the reconstruction function convolution process is defined as D13, and the convoluting reconstruction function is defined as Kernel(j), the reconstruction function convolution process is expressed as given by the following equation (7):

[Equation 7]

$$D13(\text{view},j,i) = D12(\text{view},j,i) * \text{Kernel}(j) \quad (7)$$

That is, since the independent reconstruction function convolution process can be performed for every j row of the detectors, the reconstruction function Kernel(j) can correct differences in noise characteristic and resolution characteristic for every row.

Next, at Step S6, a three-dimensional backprojection process is performed as shown in FIG. 5.

Here, the three-dimensional backprojection process is effected on the projection data D13 (view, j, i) subjected to the reconstruction function convolution process to determine backprojection data D3 (x, y, z). An image-reconstructed image is three-dimensionally image-reconstructed on an xy plane corresponding to a plane orthogonal to the z axis. A reconstruction area or plane P to be shown below is assumed to be parallel to the xy plane. The three-dimensional backprojection process will be explained later referring to FIG. 5.

Next, at Step S7, a post-process is performed as shown in FIG. 5.

Here, the post-process including image filter convolution, CT value conversion and the like is effected on the backprojection data D3 (x, y, z) to obtain a CT or tomographic image D31 (x, y).

Assuming that upon the image filter convolution process in the post-process, a tomographic image subsequent to the three-dimensional backprojection is defined as D31 (x, y, z), data subsequent to the image filter convolution is defined as D32 (x, y, z), and a two-dimensional image filter convolved on the xy plane corresponding to a tomographic image plane is defined as Filter(z), the following equation (8) is established.

[Equation 8]

$$D32(x,y,z) = D31(x,y,z) * \text{Filter}(z) \quad (8)$$

That is, since the independent image filter convolution process can be performed for every j row of the detectors, it is possible to correct differences in noise characteristic and resolution characteristic for every row.

Alternatively, an image space z-direction filter convolution process shown below may be performed after the two-dimensional image filter convolution process. The image space z-direction filter convolution process may be performed before the two-dimensional image filter convolution process. Further, a three-dimensional image filter convolution process may be performed to bring about such an effect as to share both the two-dimensional image filter convolution process and the image space z-direction filter convolution process.

Assuming that upon the image space z-direction filter convolution process, a tomographic image subjected to the image space z-direction filter convolution process is defined as D33 (x, y, z), and a tomographic image subjected to the two-dimensional image filter convolution process is defined as D32 (x, y, z), the following relation (equation 9) is established. However, v(i) becomes such a coefficient row as expressed below (in equation 10) in the form of image space z-direction filter coefficients at which the width in the z-direction is 2l+1.

[Equation 9]

$$D32(x, y, z) = \sum_{i=-l}^{l} D32(x, y, z+i) \cdot v(i) \quad (9)$$

[Equation 10]

$$v(-l), v(-l+1), \ldots v(-1), v(0), v(1), \ldots v(l-1), v(l) \quad (10)$$

Upon the helical scan, the image space filter coefficient v(i) may be an image space z-direction filter coefficient independent on a z-direction position. However, when the two-dimensional X-ray area detector 24 or the multi-row X-ray detector 24 broad in detector width as viewed in the z-direction is used in particular, the image space z-direction filter coefficient v(i) can be subjected to detailed adjustments dependent on row positions of respective tomographic images upon execution of the conventional scan (axial scan) or the cine scan if the image space z-direction filter coefficient v(i) is given as each of image space z-direction filter coefficients dependent on the positions of the rows of the X-ray detector in the z-direction. Therefore, this is further effective.

The so-obtained tomographic images are displayed on the monitor 6.

[Three-dimensional Backprojection Process]

The outline of the operation at the time that the three-dimensional backprojection process is carried out (S6 in FIG. 5) at the operation of the X-ray CT apparatus 100, is shown below.

Figure 7:
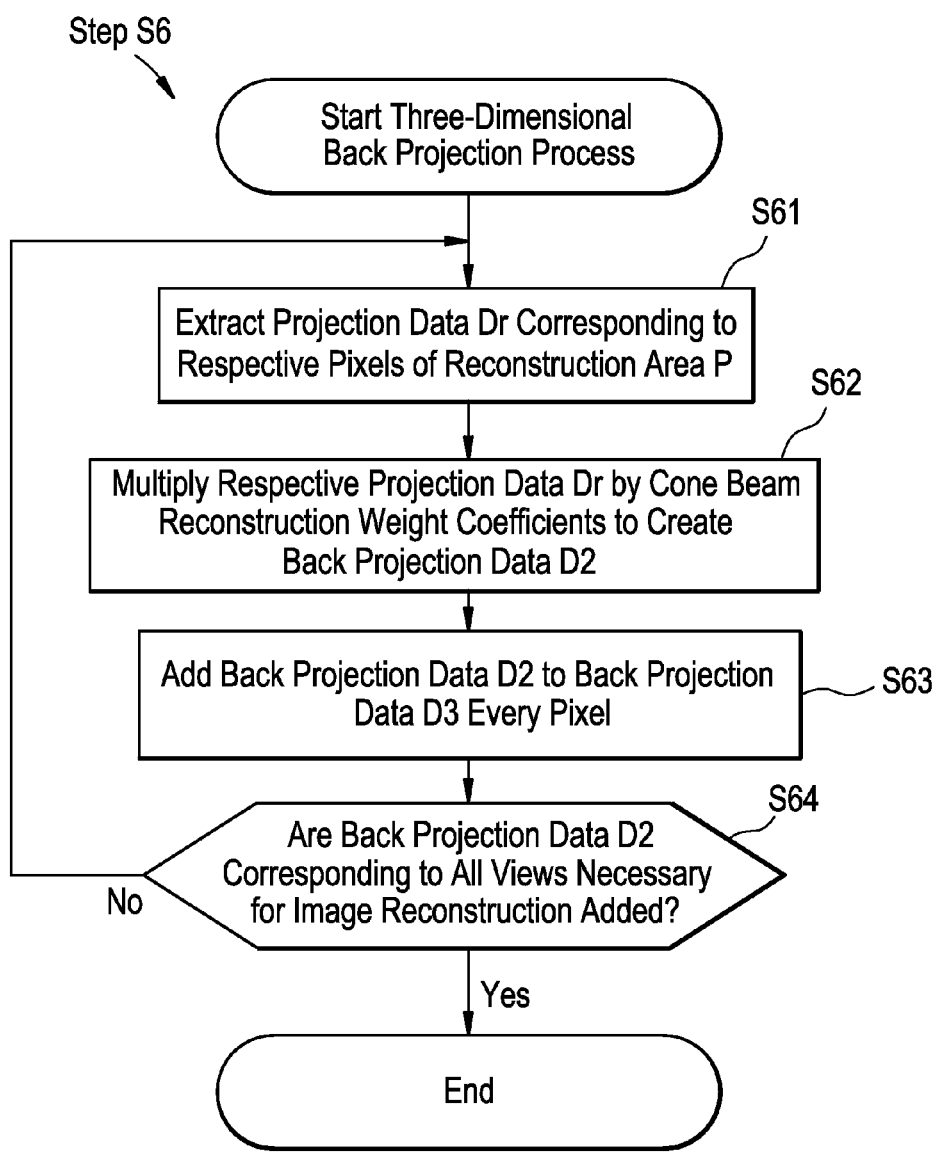
FIG. 7 is a flow chart depicting the details of a three-dimensional image reconstructing process.

FIG. 7 is a flow chart showing the details of the three-dimensional backprojection process (Step S6 in FIG. 6).

In the present embodiment, an image to be image-reconstructed is three-dimensionally image-reconstructed on an xy plane corresponding to a plane orthogonal to the z axis. That is, the reconstruction area P is assumed to be parallel to the xy plane.

At Step S61, attention is first given to one of all views (i.e., views corresponding to 360° or views corresponding to "180°+fan angles") necessary for image reconstruction of a tomographic image as shown in FIG. 7. Projection data Dr corresponding to respective pixels in a reconstruction area P are extracted.

Figure 8A:
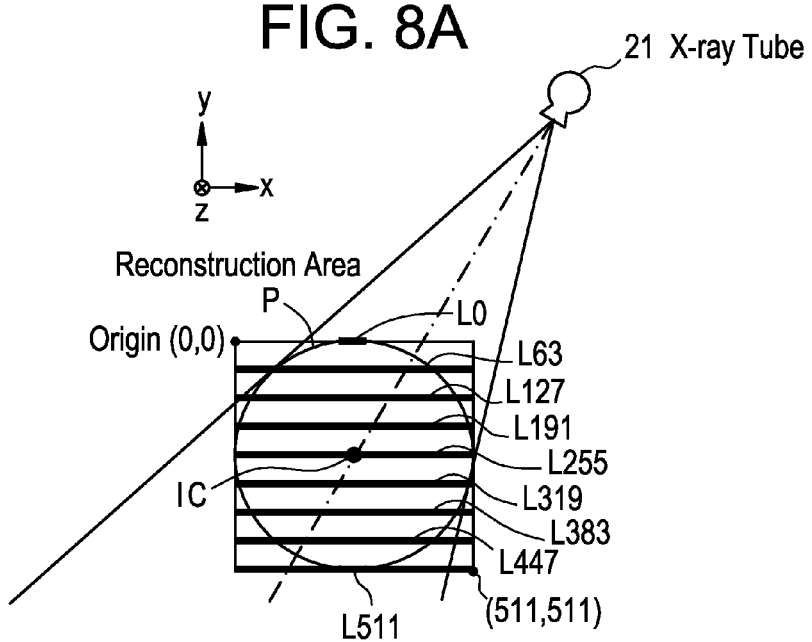
FIGS. 8a and 8b are conceptual diagrams showing a state in which lines on a reconstruction area are projected in an X-ray penetration direction.
Figure 8B:
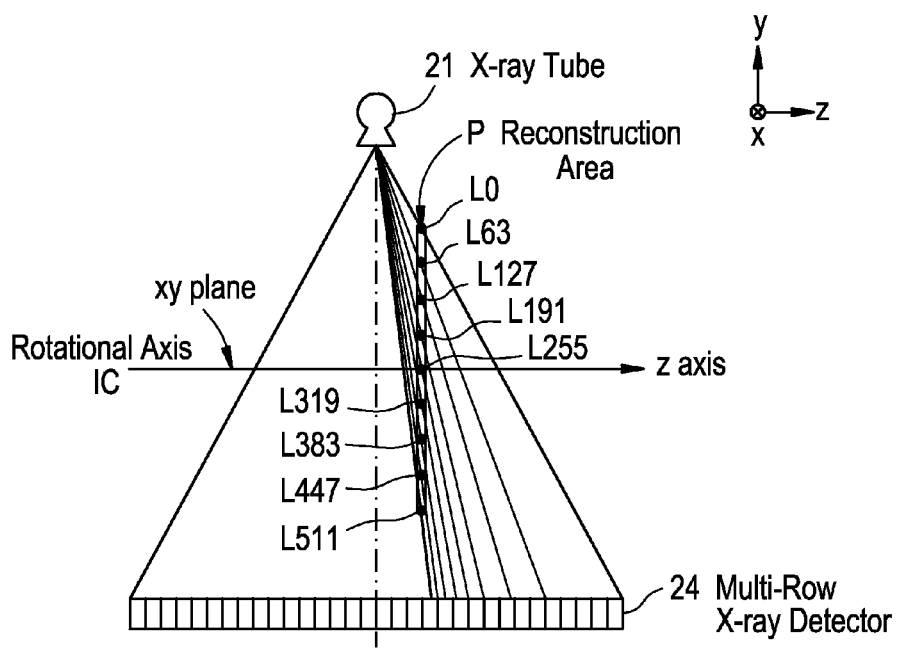
Figure 9:
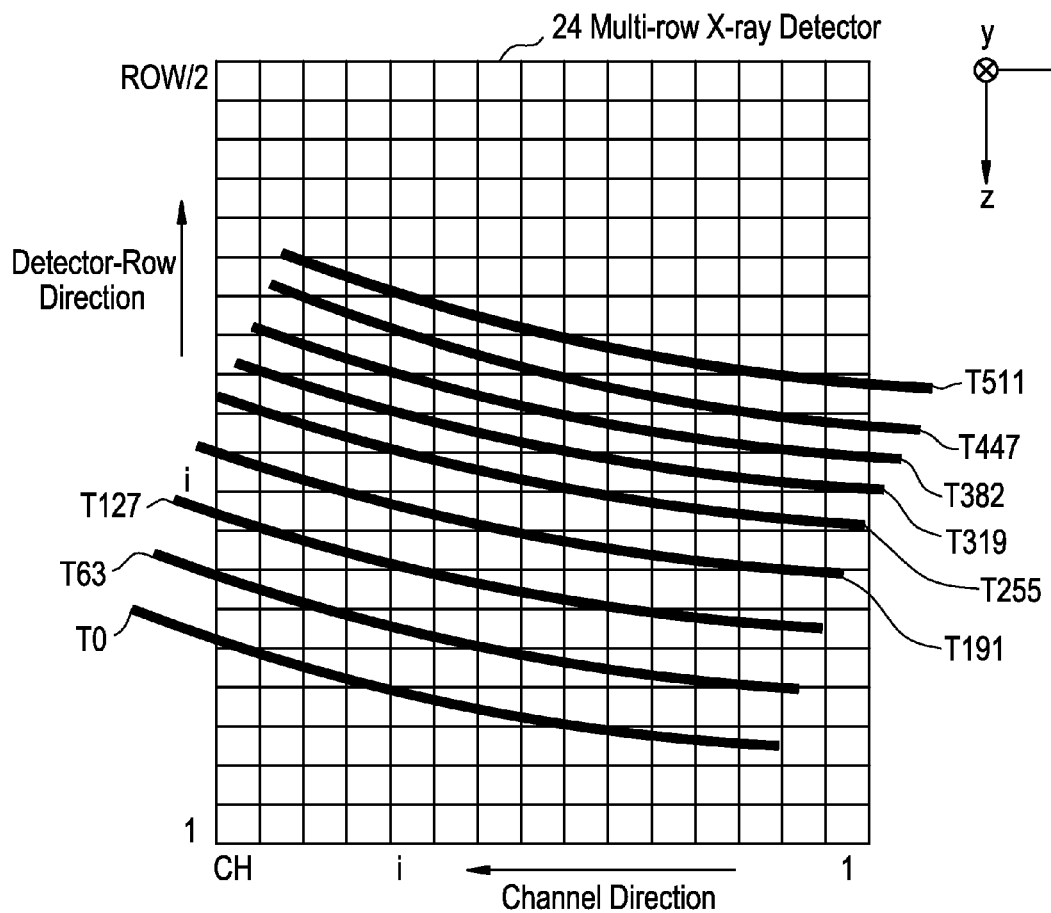
FIG. 9 is a conceptual diagram illustrating lines projected onto an X-ray detector plane.

Here, as shown in FIGS. 8(a) and 8(b), a square area of 512×512 pixels, which is parallel to the xy plane, is assumed to be a reconstruction area P. Further, a pixel row L0 parallel to an x axis of y=0, a pixel row L63 of y=63, a pixel row L127 of y=127, a pixel row L 191 of y=191, a pixel row L255 of y=255, a pixel row L319 of y=319, a pixel row L383 of y=383, a pixel row L447 of y=447, and a pixel row L511 of y=511 are taken as rows. Thus, if projection data on lines T0 through T511 obtained by projecting these pixel rows L0 to L511 on the plane of the multi-row X-ray detector 24 in an X-ray penetration direction are extracted as shown in FIG. 9, then they result in projection data Dr (view, x, y) of the pixel rows L0 to L511. However, x and y correspond to respective pixels (x, y) of the tomographic image.

The X-ray penetration direction is determined depending on geometrical positions of the X-ray focal point of the X-ray tube 21, the respective pixels and the multi-row X-ray detector 24. Since, however, the z coordinates z(view) of X-ray detector data D0 (view, j, i) are known with being added to X-ray detector data as the table linear movement z-direction position Ztable(view), the X-ray penetration direction can be accurately determined within the X-ray focal point and the data acquisition geometrical system of the multi-row X-ray detector even in the case of the X-ray detector data D0 (view, j, i) placed under acceleration and deceleration.

Incidentally, when some of lines are placed out of the multi-row X-ray detector 24 as viewed in the channel direction as in the case of, for example, the line T0 obtained by projecting, for example, the pixel row L0 on the plane of the multi-row X-ray detector 24 in the X-ray penetration direction, the corresponding projection data Dr (view, x, y) is set to "0". When it is placed outside the multi-row X-ray detector 24 as viewed in the z-direction, the corresponding projection data Dr (view, x, y) is determined by extrapolation.

Figure 10:
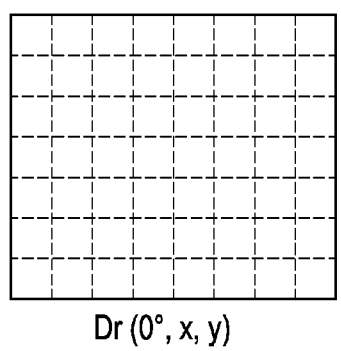
FIG. 10 is a conceptual diagram showing a state in which projection data Dr (view, x, y) are projected onto a reconstruction area.

Thus, as shown in FIG. 10, the projection data Dr (view, x, y) corresponding to the respective pixels of the reconstruction area P can be extracted.

Figure 11:
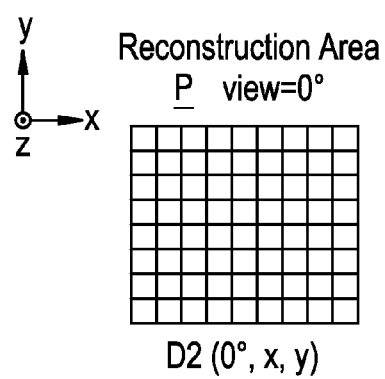
FIG. 11 is a conceptual diagram showing backprojection pixel data D2 corresponding to respective pixels on a reconstruction area.

Next, at Step S62, as shown in FIG. 7, the projection data Dr (view, x, y) are multiplied by a cone beam reconstruction weight coefficient to create projection data D2 (view, x, y) as shown in FIG. 11.

Now, the cone beam reconstruction weight function w (i, j) is as follows. Generally, when the angle which a linear line connecting the focal point of the X-ray tube 21 and a pixel g(x, y) on the reconstruction area P (xy plane) at view=βa forms with a center axis Bc of an X-ray beam is assumed to be γ and its opposite view is assumed to be view=βb in the case of fan beam image reconstruction, their relations are expressed as given by the following equation (11).

[Equation 11]

$$\beta b = \beta a + 180° - 2\gamma \quad (11)$$

When the angles which the X-ray beam passing through the pixel g(x, y) on the reconstruction area P and its opposite X-ray beam form with the reconstruction plane P, are assumed to be αa and αb respectively, they are multiplied by cone beam reconstruction weight coefficients ωa and ωb dependant on these and added together to determine backprojection pixel data D2 (0, x, y). In this case, it is given as expressed in the following equation (12)

[Equation 12]

$$D2(0,x,y) = \omega a \cdot D2(0,x,y)\_a + \omega b \cdot D2(0,x,y)\_b \quad (12)$$

where $D2(0,x,y)\_a$ is assumed to be backprojection data of view βa, and $D2(0,x,y)\_b$ is assumed to be backprojection data of view βb.

Incidentally, the sum of the cone beam reconstruction weight coefficients corresponding to the beams opposite to each other is expressed like the following equation (13):

[Equation 13]

$$\omega a + \omega b = 1 \quad (13)$$

The above addition with multiplication of the cone beam reconstruction weight coefficients ωa and ωb enables a reduction in cone angle artifact.

For example, ones determined by the following equations can be used as the cone beam reconstruction weight coefficients ωa and ωb. Incidentally, ga indicates the weight coefficient of the view βa and gb indicates the weight coefficient of the view βb. When ½ of a fan beam angle is assumed to be γmax, the following relations are established as given by the following equations (14) to (19):

[Equation 14]

$$ga = f(\gamma max, \alpha, \beta a) \quad (14)$$

[Equation 15]

$$gb = f(\gamma max, \alpha b, \beta b) \quad (15)$$

[Equation 16]

$$xa = 2 \cdot ga^q / (ga^q + gb^q) \quad (16)$$

[Equation 17]

$$xb = 2 \cdot gb^q / (ga^q + gb^q) \quad (17)$$

[Equation 18]

$$wa = xa^2 \cdot (3 - 2xa) \quad (18)$$

[Equation 19]

$$wb = xb^2 \cdot (3 - 2xb) \quad (19)$$

Here, for example, q=1.

Assuming that max [ ] are defined as functions which adopt or take the maximum values as examples of ga and gb, for example, ga an gb are given as expressed in the following equations (20) and (21).

[Equation 20]

$$ga = \max[0, \{(\pi/2 + \gamma max) - |\beta a|\} \cdot |\tan(\alpha a))| \quad (20)$$

[Equation 21]

$$gb = \max[0, \{(\pi/2 + \gamma max) - |\beta b|\} \cdot |\tan(\alpha b)) \quad (21)$$

In the case of the fan beam image reconstruction, each pixel on the reconstruction area P is further multiplied by a distance coefficient. Assuming that the distance from the focal point of the X-ray tube 21 to each of the detector row j and channel i of the multi-row X-ray detector 24 corresponding to the projection data Dr is r0, and the distance from the focal point of the X-ray tube 21 to each pixel on the reconstruction area P corresponding to the projection data Dr is r1, the distance coefficient is given as $(r1/r2)^2$.

In the case of parallel beam image reconstruction, each pixel on the reconstruction area P may be multiplied by the cone beam reconstruction weight coefficient w (i, j) alone.

Next, at Step S63, as shown in FIG. 7, the projection data D2 (view, x, y) is added to its corresponding backprojection data D3 (x, y) in association with each pixel.

Figure 12:
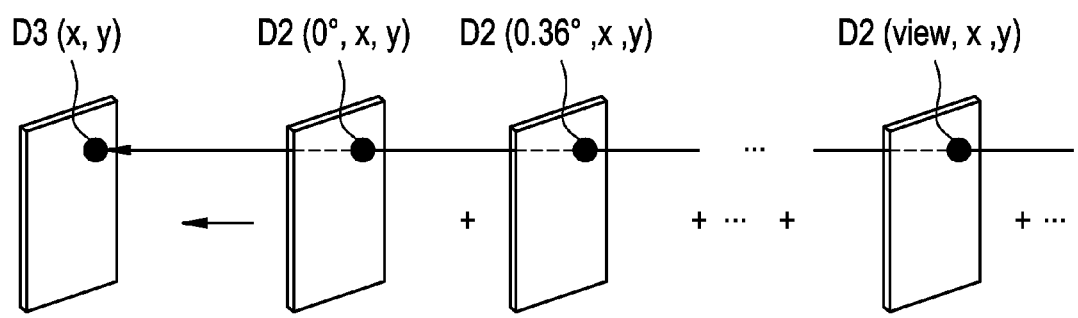
FIG. 12 is an explanatory diagram showing a state in which backprojection pixel data D2 are added together corresponding to pixels over all views to obtain backprojection data D3.

Described specifically, as shown in FIG. 12, the projection data D2 (view, x, y) is added to its corresponding backprojection data D3 (x, y) cleared in advance in association with each pixel.

Next, it is determined at Step S64 as shown in FIG. 7 whether backprojection data D2 corresponding to all views necessary for image reconstruction are added.

Here, when addition is not made to all (NO), Steps S61 through S63 are repeated with respect to all the views (i.e., views corresponding to 360° or views corresponding to "180°+fan angles") necessary for image reconstruction of the tomographic image to obtain backprojection data D3 (x, y) as shown in FIG. 12. On the other hand, when addition is made to all (Yes), the present or actual process is terminated as shown in FIG. 7.

Figure 13A:
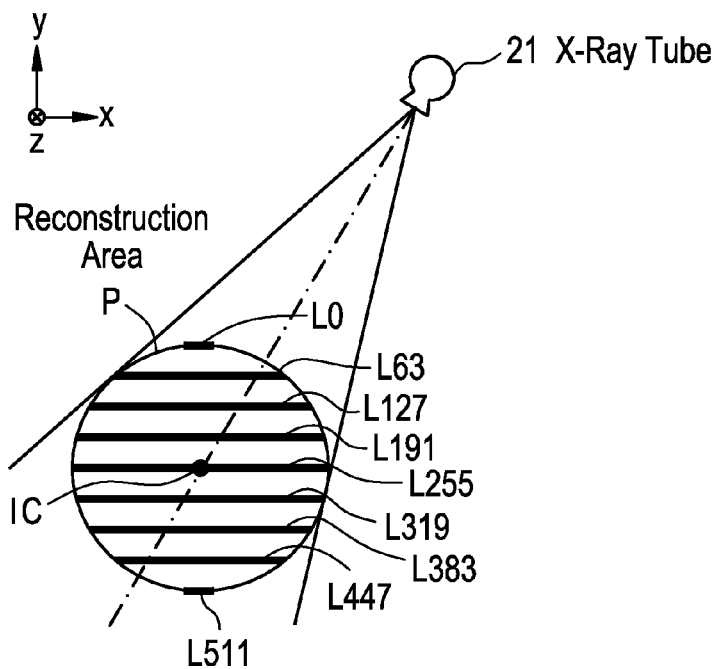
FIGS. 13a and 13b are conceptual diagrams illustrating a state in which lines on a circular reconstruction area are projected in an X-ray penetration direction.
Figure 13B:
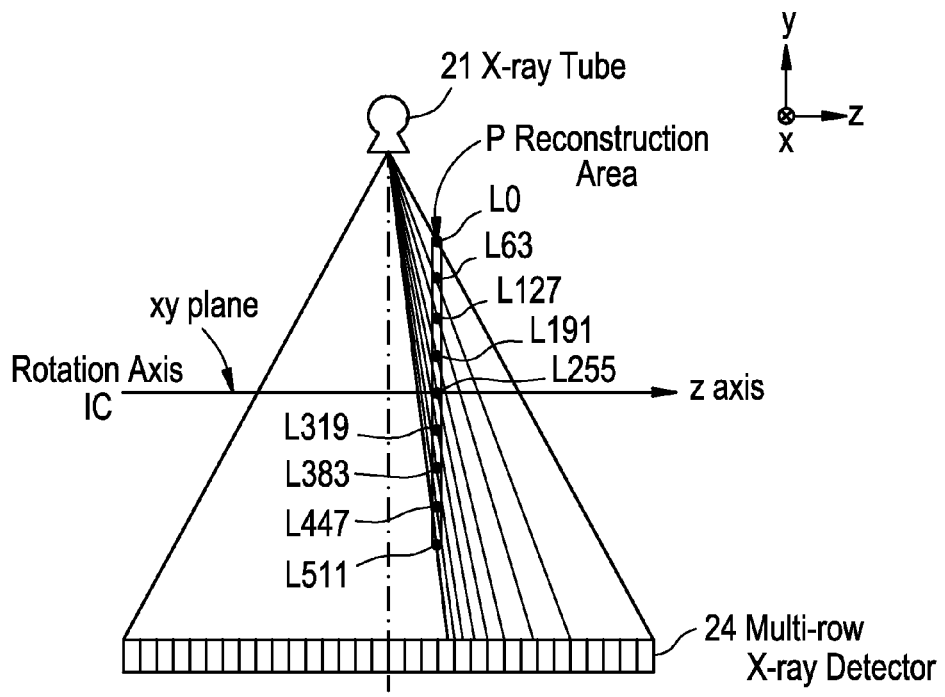

Incidentally, the reconstruction area P may be set as a circular area whose diameter is 512 pixels, without setting it as the square area of 512×512 pixels as shown in FIGS. 13(a) and 13(b).

As described above, the X-ray CT apparatus 100 includes the scanning table 10 which moves the cradle 12 placed on the subject within imaging space, the scanning gantry 20 which applies X-rays to the subject placed on the cradle 12 moved within the imaging space and performs the scan for detecting the X-rays transmitted through the subject to thereby obtain projection data, the central processing unit 3 which controls the operations of the scanning table 10 and the scanning gantry 20 to execute the scan thereby to acquire plural projection data in time-series order and image-reconstructs by calculation, a tomographic image of the subject from the projection data obtained by execution of the scan, and a monitor 6 which displays the tomographic image image-reconstructed by the central processing unit 3 on its display screen (see FIG. 1). Here, the scanning table 10 moves the subject placed on the cradle 12 along the z-direction corresponding to its body axial direction on the basis of each control signal outputted from the central processing unit 3. The scanning gantry 20 includes the X-ray tube 21 which applies X-rays from the periphery of the subject moved by the scanning table 10 to the subject so as to rotate with the direction extending along the z-direction as the axis, and the multi-row X-ray detector 24 which detects the X-rays radiated from the X-ray tube 21 and transmitted through the subject. The respective parts are controlled based on the control signals outputted from the central processing unit 3. The X-ray tube 21 applies the X-rays onto the subject such that they are brought to a cone shape spread in the channel direction extending along the direction of rotation of the X-ray tube rotated around the subject and the row direction extending along the rotational-axis direction of its rotation. In the multi-row X-ray detector 24, a plurality of X-ray detectors for detecting the X-rays radiated from the X-ray tube 21 and transmitted through the subject are arranged in matrix form so as to correspond to the channel and row directions (see FIGS. 2 and 3).

Upon photographing the subject by using the X-ray CT apparatus 100, the operator inputs the condition for performing the actual scan on the subject to the input device 2.

Next, the central processing unit 3 sets parameters for operating the scanning gantry 20 and the scanning table 10 upon execution of the actual scan, based on the condition inputted to the input device 2.

Here, the central processing unit 3 sets the parameters for operating the respective parts, using the so-called X-ray automatic exposure function in such a manner that the actual scan is effected on the subject by the helical scan system, for example.

In the present embodiment, when the actual scan is first effected on the subject at such a helical pitch as to correspond to first helical pitch set data H1, based on the condition inputted to the input device 2 as shown in FIG. 17(*b*), the central processing unit 3 calculates respective X-ray tube current values supplied to the X-ray tube 21 at respective positions for obtaining X-ray projection data in a body axial direction of the subject and view directions around the subject. The storage device 7 stores the calculated values therein as first tube current set data A1. For example, after a sectional area of the subject and its sectional shape are determined based on a scout image of the subject photographed before execution of the actual scan, the central processing unit 3 calculates X-ray tube current values supplied to the X-ray tube 21 at respective positions upon execution of the actual scan in such a way as to correspond to the determined sectional area and second shape and defines the calculated X-ray tube current values as first tube current set data A1. Next, the central processing unit 3 determines whether the respective X-ray tube current values set as the first tube current set data A1 are within a reference or standard range S adaptable to the X-ray tube 21. When they are within the standard range S at that time, the central processing unit 3 decides the first tube current set data A1 as a set value supplied to the X-ray tube 21 upon the actual scan. On the other hand, when the first tube current set data A1 contains the X-ray tube current values not within the standard range S as shown in FIG. 17(*b*), the central processing unit 3 adjusts the same so as to bring X-ray tube current values at a portion a not within the standard range S at the first tube current set data A1 to the values within the standard range S without deciding the X-ray tube current values related to the first tube current set data 1 as the set values supplied to the X-ray tube 21 upon the actual scan thereby to change the first tube current set data A1 to second tube current set data A2, which in turn is stored in the storage device 7. When each X-ray tube current value exceeds the upper limit value of the standard range S as shown in FIG. 17(*b*) for example, the X-ray tube current value lying in the portion a not within the standard range S is adjusted to be close to the upper limit value. The central processing unit 3 determines the respective X-ray tube current values related to the second tube current set data A2 as set values for the X-ray tube current values supplied to the X-ray tube 21 upon the actual scan. Along with it, as shown in FIG. 17(*b*), the set value of a helical pitch at the portion a to which the X-ray tube current values not within the standard range S at the first tube current set data A1 are set, is adjusted so as to correspond to the ratio between each of the X-ray tube current values related to the first tube current set data A1 and each of the X-ray tube current values related to the second tube current set data A2. With its adjustment, the central processing unit 3 changes first helical pitch set data H1 to second helical pitch set data H2 and causes the storage device 7 to store it therein. The central processing unit 3 determines the second helical pitch set data H2 as the set value of the helical pitch at the actual scan. Thus, the central processing unit 3 used as a computer sets the parameters including the X-ray tube current values and the helical pitches by data processing thereof.

Next, the operations of the scanning gantry 20 and the scanning table 10 are controlled by the central processing unit 3 based on the set parameters to scan the subject, thereby obtaining X-ray projection data.

Next, the central processing unit 3 image-reconstructs a tomographic image of the subject, based on the so-obtained X-ray projection data. Then, the monitor 6 displays the tomographic image on its display screen.

Thus, in the present embodiment, the X-ray tube current values supplied to the X-ray tube 21 are set by the X-ray automatic exposure function upon execution of the actual scan. Thereafter, when the X-ray tube current values set by the X-ray automatic exposure function are not within the standard range of the X-ray tube current values settable at the X-ray tube 21, the X-ray tube current values at the portion not within the standard range are changed so as to be within the standard range, and the set value of each helical pitch is changed so as to correspond to the ratio between each of the pre-change X-ray tube current values and each of the post-change X-ray tube current values. Therefore, in the present embodiment, even when the X-ray tube current values set by the X-ray automatic exposure function are not within the standard range of the X-ray tube current values settable at the X-ray tube 21, a tomographic image similar in image quality to the tomographic image obtained by execution of the scan at the X-ray tube current values set by the X-ray automatic exposure function can be obtained. Thus, in the present embodiment, the image quality of the tomographic image continuous in the z-direction can be uniformized and more optimized.

Second Embodiment

A second embodiment according to the present invention will be explained below.

The first embodiment shows the example in which the optimum image quality can be obtained by adjusting the helical pitch corresponding to one of parameters exerted on the image quality with respect to the range in which the set value of the X-ray tube current in the z-direction has exceeded the upper limit value, even when the set value of the X-ray tube current is set to within a range not greater than the upper limit value. On the other hand, the present embodiment shows an example in which even when a set value of an X-ray tube current is set to within a range not greater than an upper limit value, the optimum image quality can be obtained by adjusting channel direction filtering corresponding to one of parameters exerted on other image quality.

Except for this point, the present embodiment is similar to the first embodiment. Therefore, dual portions will not be explained.

Figure 19A:
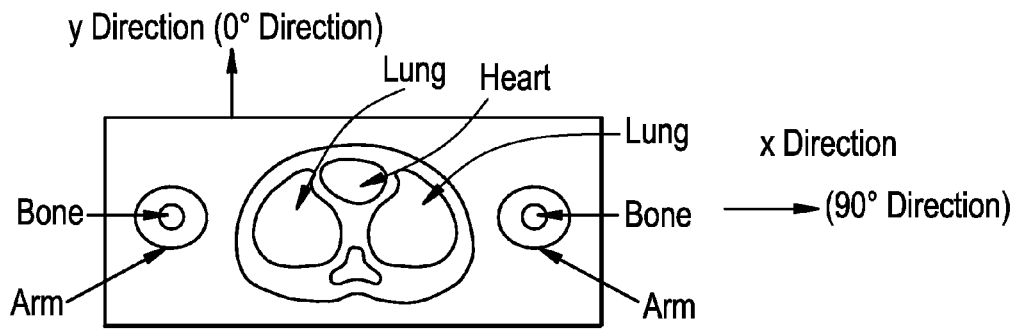
FIG. 19(a) is a diagram showing a tomographic image about a region including arms of a subject and its lung field.

FIG. 19(*a*) shows a tomographic image of a portion that contains arms and a lung field in a subject.

In such a case, with a view to more uniformizing noise of X-ray projection data in respective view directions, there is a need to supply a larger X-ray tube current to an X-ray tube 21 as viewed in a 90° direction corresponding to an x direction in order to bring image noise of X-ray projection data in a 0° direction corresponding to a y direction and image noise of X-ray projection data in the 90° direction corresponding to the x direction.

That is, as shown in FIG. 16(*b*), there is a need to change the X-ray tube current in the xy plane.

Figure 19B:
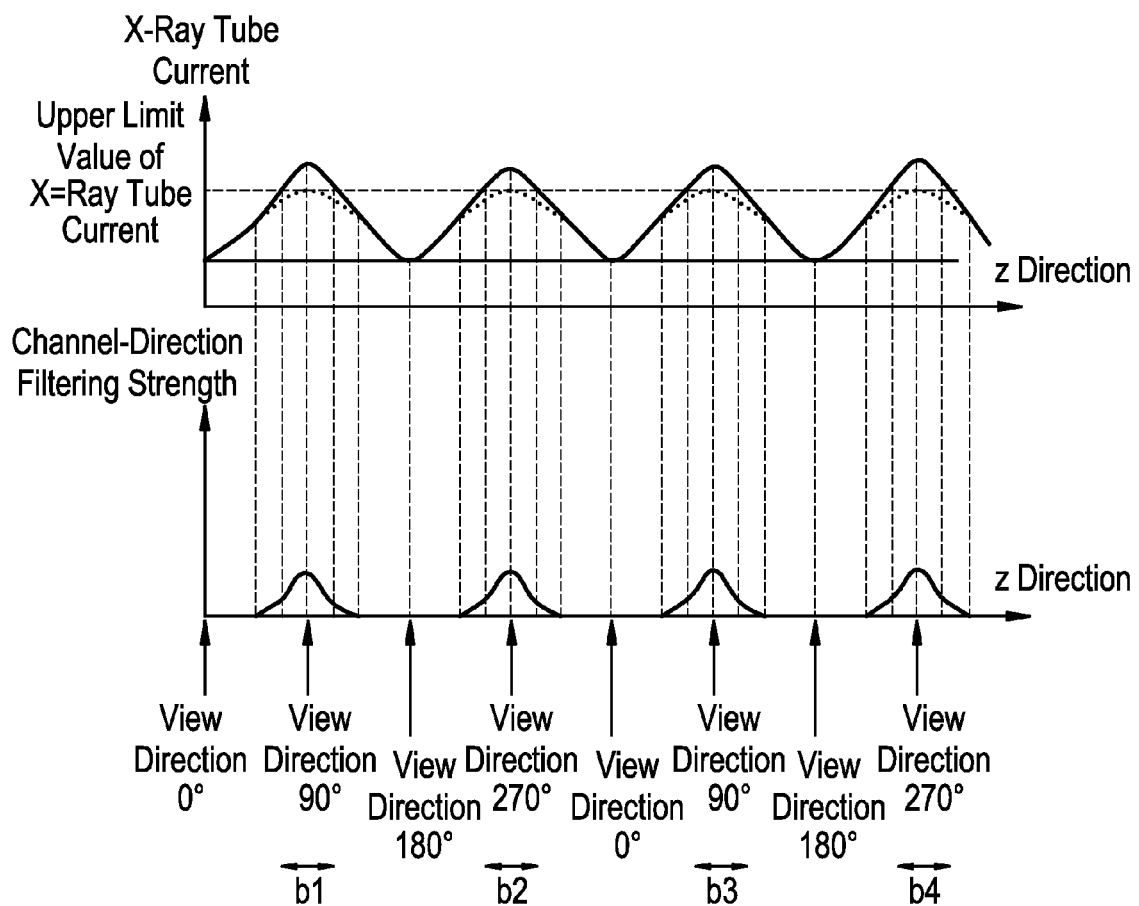
FIG. 19(b) is a diagram showing adjustments to X-ray tube current values by channel-direction filtering.

In this case, a larger X-ray tube current is required as seen in each of view directions 90° and 270° as shown in FIG. 19(b). It is preferable to effect a channel-direction filtering process on ranges b1, b2, b3 and b4 in which X-ray tube currents to be determined have exceeded an upper limit of an X-ray tube current value, and X-ray projection data obtained in the vicinity of the ranges as shown in FIG. 19(b). Here, the strength of channel-direction filtering can be adjusted in advance in such a manner that X-ray projection data short in X-ray tube current and deteriorated in S/N without the X-ray tube current being not capable of being set to the upper lime value or more are improved in S/N, and image noise of a tomographic image obtained for the last time can achieve a noise index. Described specifically, when an X-ray tube current outputtable corresponding to the required X-ray tube current is small, the strength of the channel-direction filtering is greatly adjusted to more convolve X-ray projection data at adjacent channels, whereby a noise improvement in X-ray projection data is made. Therefore, noise developed in each tomographic image is reduced by the X-ray projection data obtained in the ranges b1, b2, b3 and b4. When the X-ray tube current outputtable corresponding to the required X-ray tube current is acceptably large in reverse, the strength of the channel-direction filtering is adjusted low to less convolve the X-ray projection data at the adjacent channels, thereby leading to a nose improvement in X-ray projection data. Therefore, noise developed in each tomographic image is reduced by the X-ray projection data obtained in the ranges b1, b2, b3 and b4. Here, when an X-ray tube current lying within a range of X-ray tube currents outputtable at respective times from the X-ray tube is required, the central processing unit 3 determines that the set value of the corresponding X-ray tube current can be outputted from the central processing unit 3 to the X-ray controller 22 via the control controller 29.

On the other hand, when an X-ray tube current out of the range of the X-ray tube currents outputtable at the respective times from the X-ray tube is requested, the central processing unit 3 judges that the set value of the corresponding X-ray tube current cannot be outputted from the central processing unit 3 to the X-ray controller 22 via the control controller 29.

This adjustment can determine in advance, the strength of channel-direction filtering with respect to longitudinal views, i.e., views where the determined X-ray tube current has exceeded the upper limit of the X-ray tube current value, from an oval ratio about a subject's section predicted based on the scout image. Thus, a rise in X-ray tube current value can be prevented by more enhancing the strength of the channel-direction filtering at a z-direction coordinate position where a larger X-ray tube current value has been determined in particular, or as seen in a view direction. That is, changing the strength of the channel-direction filtering as shown in FIG. 19(b) makes it possible to reduce a set value of an X-ray tube current indicated by a solid line T0 a set value of an X-ray tube current indicated by a dotted line.

Thus, in a manner similar to the first embodiment, the present embodiment can obtain a tomographic image similar in image quality to a tomographic image obtained by executing a scan at each X-ray tube current value set by the X-ray automatic exposure function even where the X-ray tube current values set by the X-ray automatic exposure function are not within the standard range of the X-ray tube current values settable at the X-ray tube 21. Thus, the present embodiment can improve the image quality of each tomographic image while ensuring the uniformity of the image quality of the tomographic image continuous in the z-direction.

Incidentally, control on the X-ray tube current and control on the strength of the channel-direction filtering in the second embodiment can be applied even to a helical scan and a cine scan. If one rotation is taken into consideration, then they can be applied even to a conventional scan (axial scan).

Third Embodiment

A third embodiment according to the present invention will be explained below.

Each of the first and second embodiments has described where the image quality in the z-direction is optimized at the helical scan or the conventional scan (axial scan) or cine scan continuous in the z-direction.

In the present embodiment, each X-ray tube current is optimized in consideration of a helical pitch at a variable-pitch helical scan or a helical shuttle scan and changes in the number of rotations for projection data used in image reconstruction.

Except for this point, the present embodiment is similar to the first and second embodiments. Therefore, dual portions will not be explained.

Figure 21:
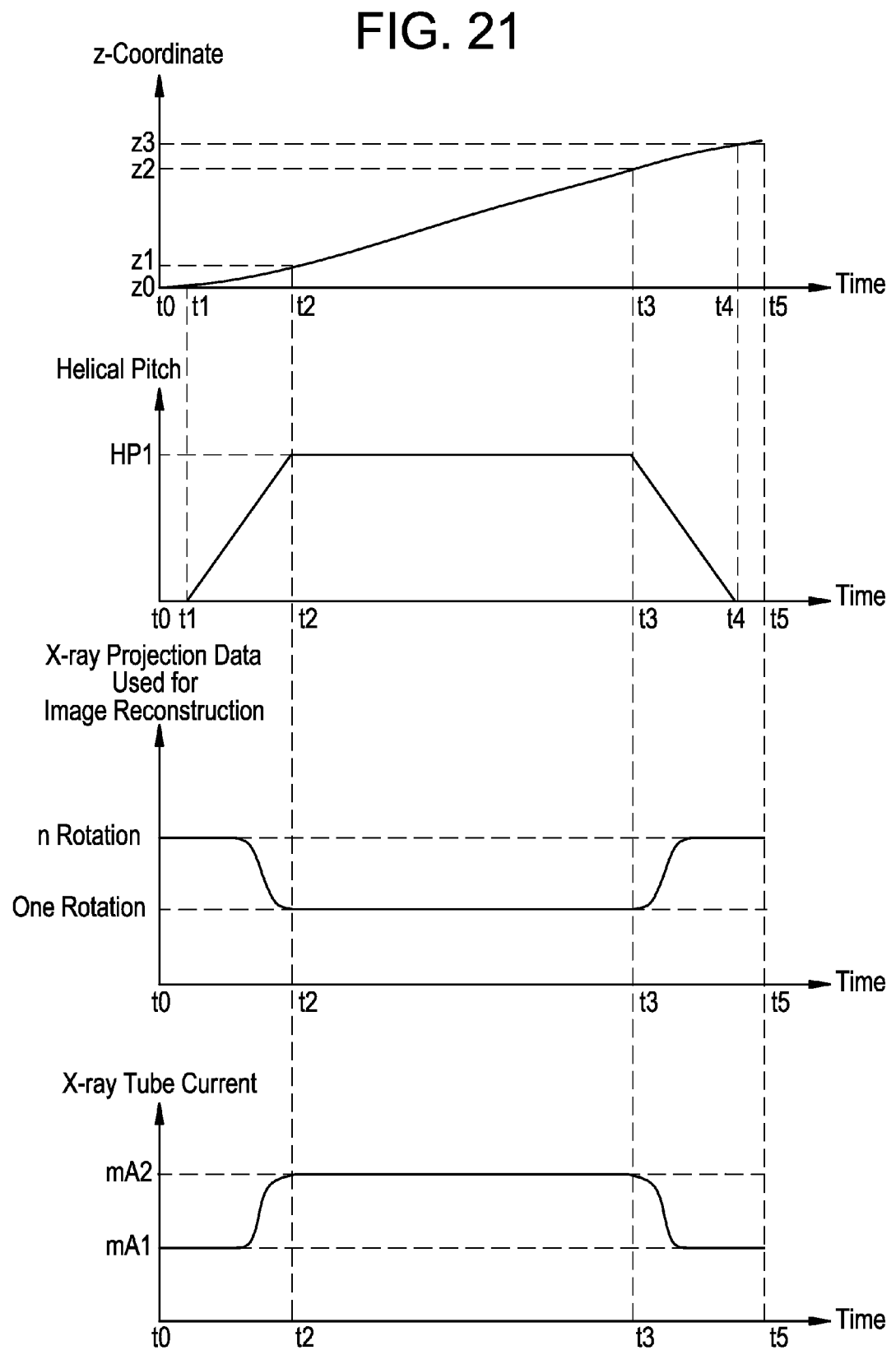
FIG. 21 is a diagram illustrating an example 2 of a relationship between a helical pitch, the number of rotations for used data and X-ray tube currents at a variable-pitch helical scan or a helical shuttle scan.
Figure 22:
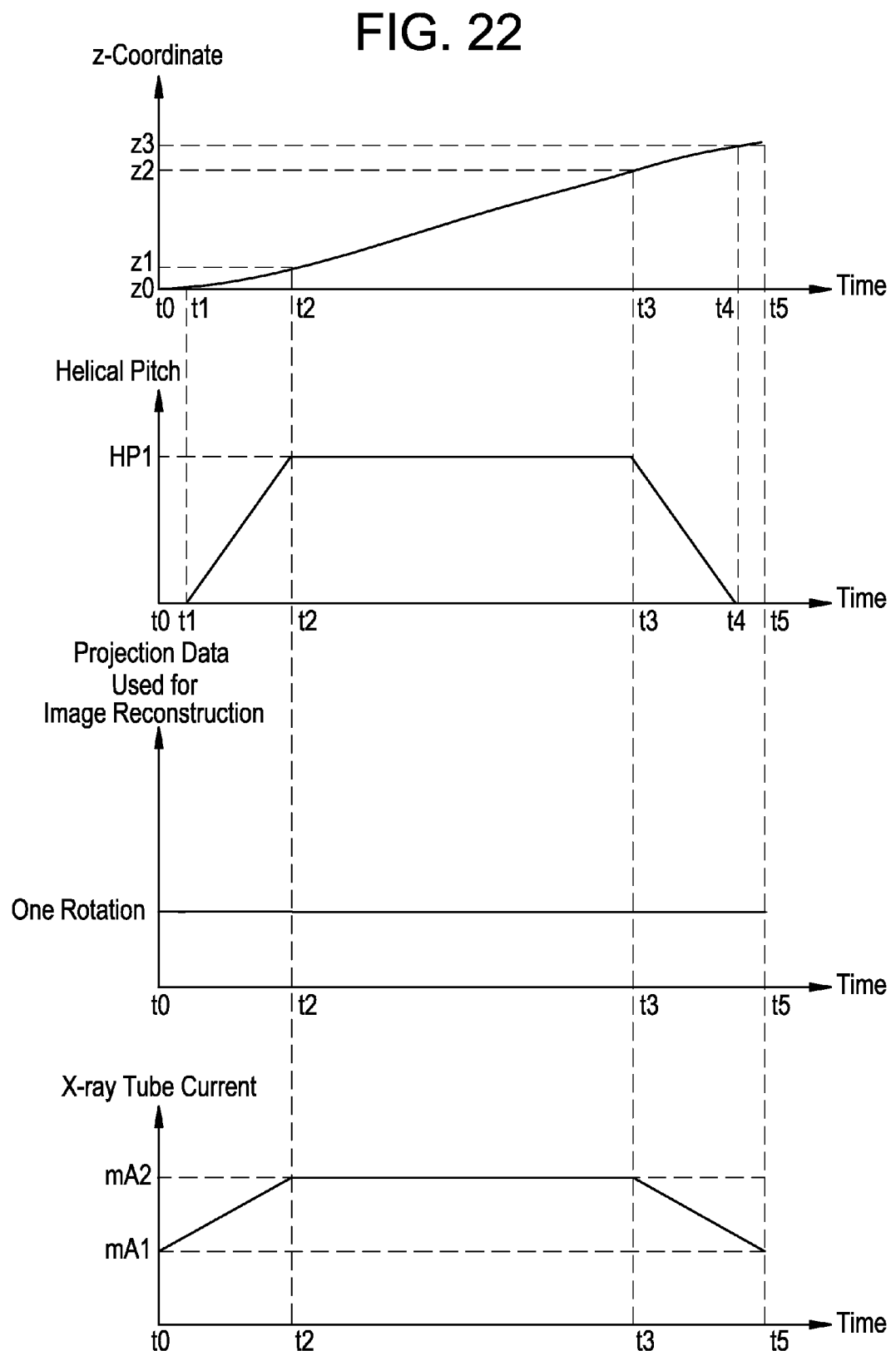
FIG. 22 is a diagram depicting an example 3 of a relationship between a helical pitch, the number of rotations for used data and X-ray tube currents at a variable-pitch helical scan or a helical shuttle scan.

FIGS. 20, 21 and 22 are respectively diagrams showing a relationship between a helical pitch, the number of rotations for used data and X-ray tube currents at a variable-pitch helical scan or a helical shuttle scan.

As shown in FIGS. 20, 21 and 22, the helical pitch is changed in a z-direction or in a time t direction at the variable-pitch helical scan or the helical shuttle scan. At a start point z0 and a stop point z3 in particular, the helical pitch is set to 0. That is, at the start point z0 and the stop point z3, a scanning table or an X-ray data acquisition system is caused to stay for a given definite period of time. When the image reconstruction is done upon acceleration and deceleration of the scanning table or the X-ray data acquisition system, S/N can be improved by using X-ray projection data over one rotation.

When the variable-pitch helical scan or the helical shuttle scan is executed as shown in FIG. 20, a central processing unit 3 causes the scanning table to stay between times t0 and t1 while it remains located at z0 as viewed in the z-direction. During a period from the times t1 and t2, the scanning table is accelerated and moved between z0 to z1 as viewed in the z-direction. During a period from the times t2 and t3, the scanning table is moved at a constant speed between z1 and z2 as viewed in the z-direction. During a period from the times t3 to t4, the scanning table is moved between z2 and z3 as viewed in the z-direction while it is being decelerated. During a period from the times t4 to t5, the scanning table is caused to stay while it remains located at z3 as viewed in the z-direction.

As shown in FIG. 20, the helical pitch is set to 0 between the times t0 and t1. Thereafter, a cradle 12 of the scanning table 10 is accelerated between the times t1 and t2, and the helical pitch is set to 1 between the times t2 and t3. Then, the cradle 12 of the scanning table 10 are decelerated between the times t3 and t4, and the helical pitch is set to return to 0 between the times t4 and t5.

While the X-ray projection data used for image reconstruction is used under one rotation at the time t0 as shown in FIG. 20, the X-ray projection data at the maximum value n rotation (n>1) is used midway between the times t0 and t2 and the X-ray projection data is returned to the one rotation at the time t2.

The X-ray projection data used for image reconstruction is constant under one rotation between the times t2 and t3. While the X-ray projection data used for image reconstruction is used under one rotation at the time t3, the X-ray projection data at the maximum value n rotation is used midway between the times t3 and t5. At the time t5, the X-ray projection data used for image reconstruction is finally returned to the one rotation. At a portion where the helical pitch is not greater than 1 in particular, the range of the X-ray projection data used for image reconstruction can be defined greater and the image quality can be improved. This becomes effective in particular upon acceleration/deceleration of the helical shuttle scan and the variable-pitch helical scan. Incidentally, the above term "X-ray projection data at n rotation" means "X-ray projection data obtained by rotating a data acquisition system constituted of an X-ray tube 21 and a multi-row X-ray detector 24 about the subject by n orbits upon scanning the subject". The term "X-ray projection data used for image reconstruction is used at one rotation" means that "the image reconstruction is carried out using X-ray projection data obtained by rotating the X-ray tube 21 about the subject by one rotation upon scanning the subject".

In such a case, in order to make a method for reconstructing an image and its image quality closer to the image reconstruction at the normal conventional scan (axial scan) in the neighborhood of the times t0 and t5 and make a method for reconstructing an image and its image quality close to the image reconstruction at the normal helical scan between the times t2 and t3, X-ray projection data used for image reconstruction are set to one rotation between the times t0 and t5 and between the times t2 and t3.

The X-ray tube current is controlled such that the image quality becomes constant between the times t0 and t5. As shown in FIG. 20, the X-ray tube current is set to mA2 (mA2>mA1) greater than mA1 at the time t0 and set to be mA1 indicative of an X-ray tube current corresponding to the minimum value midway between the times t0 and t2. At the time t2, the X-ray tube current is set to return to mA1 greater than mA1.

Thereafter, the X-ray tube current is set constant as mA2 greater than mA1 between the times t2 and t3. Then, the X-ray tube current is set to be mA1 corresponding to the X-ray tube current indicative of the maximum value midway between the times t3 and t5. At the time t5, the X-ray tube current is set to return to mA2 greater than mA1.

Incidentally, a helical pitch HP, an X-ray tube current mA and a view angle range L of X-ray projection data used for image reconstruction are adjusted so as to satisfy the relation expressed below (in the following equation 22) between the times t0 and t2 and between the times t3 and t5. Thus, constant image quality is obtained in the z-direction.

Incidentally, here, the term "the view angle range L of X-ray projection data used for image reconstruction" indicates an angular range from a start angle for a view angle of X-ray projection data used for image reconstruction to an end angle for the view angle of X-ray projection data used for image reconstruction. This is set based on the angel between the end angle and the start angle.

[Equation 22]

$$\frac{mA \cdot L}{HP} = Const \text{ (constant)} \qquad (22)$$

That is, the constant image quality is obtained in the z-direction by controlling the product of the X-ray tube current mA and the view angle range L of X-ray projection data and the ratio between the helical pitches to be constant or approximately constant.

Upon the variable-pitch helical scan or the helical shuttle scan, the central processing unit 3 sets the scanning table in such a manner that it stays at z0 between times t0 and t1 at a z coordinate as shown in FIG. 21. Then, the central processing unit 3 sets the scanning table in such a manner that it is moved while being accelerated between z0 and z1 in the z-direction during a period from the times t1 to t2. Between the times t2 and t3, the central processing unit 3 sets the scanning table in such a way that it is moved at a constant speed between z1 and z2 in the z-direction. Between the times t3 and t4, the central processing unit 3 sets the scanning table in such a manner that it is moved while being decelerated between z2 and z3 in the z-direction. Further, the central processing unit 3 sets the scanning table in such a manner that it stays at z3 as viewed in the z-direction between the times t4 and t5.

In such a case, the helical pitch is set to 0 between the times t0 and t1 as shown in FIG. 21. The cradle 12 of the scanning table 10 is accelerated between the times t1 and t2. Between the times t2 and t3, the helical pitch HP is held constant as 1, for example. The cradle 12 of the scanning table 10 is decelerated between the times t3 and t4, and the helical pitch is returned to 0 between the times t4 and t5.

The X-ray projection data used for image reconstruction is reduced from n rotation to one rotation between the times t0 and t2. Then, the X-ray projection data is set so as to be constant under one rotation between the times t2 and t3. Further, the X-ray projection data is set so as to increase from one rotation to n rotation between the times t3 and t4.

Therefore, a larger amount of X-ray projection data are used between the times t0 and t2 and between the times t3 and t4 to improve the image quality. Therefore, the X-ray tube current can be reduced between the times t0 and t2 and between the times t3 and t4 to hold the image quality constant between the times t0 and t4. At a portion in which the helical pitch is not greater than 1 in particular, the range of the X-ray projection data used for image reconstruction can be defined greater and the image quality can hence be improved. This becomes effective particularly upon acceleration/deceleration of the helical shuttle scan and the variable-pitch helical scan.

Thus, assuming that mA>mA1 as shown in FIG. 21, the X-ray tube current is set to a small X-ray tube current mA1 at the time t0. Between the times t0 and t2, the X-ray tube current is increased from the small X-ray tube current mA1 to an X-ray tube current mA2 larger than mA1. At the time t2, the X-ray tube current is set so as to be the large X-ray tube current mA2. Between the times t2 and t3, the X-ray tube current is set so as to be constant at the large X-ray tube current mA2. Between the times t3 and t5, the X-ray tube current is decreased from the large X-ray tube current mA2 to the small X-ray tube current mA1.

Incidentally, a helical pitch HP, an X-ray tube current mA and a view angle range L of X-ray projection data used for image reconstruction are controlled in accordance with the above relation (the following equation 22) between the times t0 and t2 and between the times t3 and t5. Thus, constant image quality is obtained in the z-direction in a manner similar to the above case.

That is, the constant image quality is obtained in the z-direction by adjusting the product of the X-ray tube current mA and the view angle range L of X-ray projection data and the ratio between the helical pitches to be constant or approximately constant.

In such a case, projection data used for image reconstruction is set to one rotation between the times t2 and t3 in order to approach the image reconstruction for the normal helical scan between the times t2 and t3. Between the times t0 and t2 and between the times t3 and t5, the speed at which the cradle 12 of the scanning table 10 travels in the z-direction, which is defined as a relative speed for the scanning table and the data acquisition system, becomes further slow as it approaches the times t0 and t5.

Therefore, X-ray projection data at n rotation is used for image reconstruction at the times t0 and t5 in order to further improve image noise without increasing a slice thickness corresponding to the thickness of a tomographic image as viewed in the z-direction, i.e., reducing resolution in the z-direction, of the tomographic image.

Upon the variable-pitch helical scan or the helical shuttle scan, the central processing unit 3 sets the scanning table in such a manner that it stays at z0 at a z coordinate between the times t0 and t1 as shown in FIG. 22. Between the times t1 and t2, the scanning table moves while being accelerated between z0 and z1 at the z coordinate. Between the times t2 and t3, the central processing unit 3 moves the scanning table at a constant speed between z1 and z2 at the z coordinate. Then, the central processing unit 3 moves the scanning table between the times t3 and t4 while it is being decelerated between z2 and z3 at the z coordinate. Between the times t4 and t5, the central processing unit 3 causes the scanning table to stay at z3.

The helical pitch is set to 0 between the times t0 and t1. The cradle 12 of the scanning table 10 is accelerated between the times t1 and t2. Between the times t2 and t3, the helical pitch HP is set so as to be constant as 1. The cradle 12 of the scanning table 10 is decelerated between the times t3 and t4, and the helical pitch HP is set to return to 0 between the times t4 and t5.

Between the times t0 and t5, X-ray projection data used for image reconstruction is held constant and set to one rotation. In this case, a view angle range for X-ray projection data used for the image reconstruction of the used X-ray projection data is held constant in such a manner that priority is given to keeping time resolution of a tomographic image constant.

Therefore, the X-ray tube current is set to a small X-ray tube current mA1 at a time t0 as shown in FIG. 22 such that image quality is held constant between the times t0 and t4. The X-ray tube current is increased from the small X-ray tube current mA1 to a large X-ray tube current mA2 between the times t0 and t2. Incidentally, at this time, the X-ray tube current also increases as the helical pitch becomes larger. Here, it may preferably be controlled in such a manner that the ratio between the helical pitch and the X-ray tube current becomes constant or approximately constant. At the time t2, the X-ray tube current is set as the large X-ray tube current mA2, and the X-ray tube current mA2 is kept constant between the times t2 and t3. At the time t3, the X-ray tube current is set as the X-ray tube current mA2 and reduced from the large X-ray tube current mA2 to the small X-ray tube current mA1 between the times t3 and t5. Incidentally, at this time, the X-ray tube current is also reduced as the helical pitch becomes smaller. Here, it may preferably be controlled in such a manner that the ratio between the helical pitch and the X-ray tube current becomes constant or approximately constant. At the time t5, the X-ray tube current is returned to the small X-ray tube current mA1.

Thus, the central processing unit 3 adjusts the X-ray tube current in such a manner that the image quality of the tomographic image approaches image quality obtained by the normal conventional scan or the helical scan as shown in FIG. 20. As shown in FIG. 21, the central processing unit 3 adjusts the X-ray tube current such that the exposure of X-rays is more reduced upon acceleration/deceleration. Further, the central processing unit 3 adjusts the X-ray tube current in such a manner that the quality of the tomographic image is maintained as it is. As shown in FIG. 22, the central processing unit 3 adjusts the X-ray tube current in such a manner that time resolution of the tomographic image is held constant.

In the above example, control on the helical pitch corresponding to a parameter for image quality of the tomographic image and on a parameter for the amount of data used in the image reconstruction is adjusted preferentially in the first place and thereafter the X-ray tube current is adjusted. Thus, in order to adapt to a change table of the X-ray tube current values in the z-direction obtained from the scout image, the parameter for controlling the image quality of the tomographic image, which is called X-ray tube current, is used in the first place. In addition to this case, a parameter other than the X-ray tube current, for controlling other image quality is adjusted on a preferential basis. The change table of the z-direction X-ray tube current values from the scout image firstly obtained by adjustments to those parameters is corrected and thereafter the X-ray tube current is adjusted, whereby the automatic exposure function of the X-ray CT apparatus can also be realized.

A flow of processing for each of the embodiments shown in FIGS. 20, 21 and 22 will be shown below.

Figure 23:
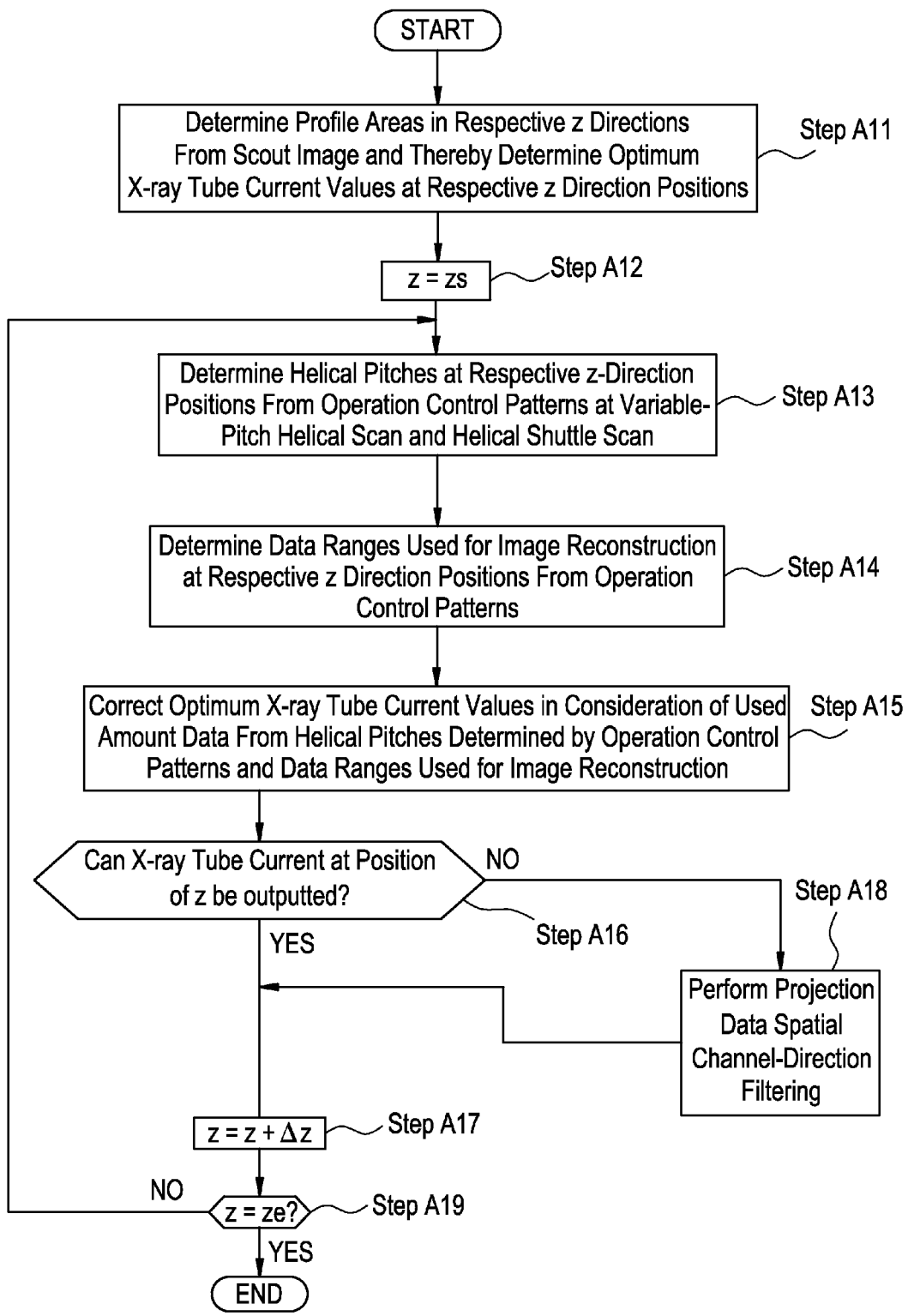
FIG. 23 is a diagram showing an X-ray automatic exposure function for determining an X-ray tube current in consideration of the amount of data used for image reconstruction.

Upon the variable-pitch helical scan or the helical shuttle scan executed in each of the embodiments shown in FIGS. 20, 21 and 22, the central processing unit 3 executes each processing as shown in FIG. 23.

At Step A11, as shown in FIG. 23, profile areas in respective z-directions are determined from a scout image, and the optimum X-ray tube current values at respective z-direction positions are determined.

Next, at Step A12, z=zs as shown in FIG. 23. However, a z-direction start coordinate is defined as zs.

Next, at Step A13, as shown in FIG. 23, helical pitches at the respective z-direction positions are determined from operation control patterns at the variable-pitch helical scan and the helical shuttle scan.

Next, at Step A14, as shown in FIG. 23, data ranges used for image reconstruction at the respective z-direction positions are determined from the operation control patterns.

Next, at Step A15, as shown in FIG. 23, the optimum X-ray tube current values are corrected in consideration of the used amount of data by or from the helical pitches determined by the operation control patterns and the data ranges used for image reconstruction.

Next, at Step A16, as shown in FIG. 23, it is determined whether an X-ray tube current at the position of z can be outputted. If the answer is found to be YES, then the processing proceeds to Step A17. If the answer is found to be NO, then the processing proceeds to Step A18.

Next, at Step A17, z=z+Δz as shown in FIG. 23.

Next, at Step A18, projection data spatial channel-direction filtering is done as shown in FIG. 23.

Next, at Step A19, it is determined whether z≧ze as shown in FIG. 23. If the answer is found to be YES, then the processing is terminated. If the answer is found to be NO, then the processing is returned to Step A13. However, a z-direction end coordinate is defined as ze.

Incidentally, each example referred to above can bring about a similar effect even when a parameter for image quality other than the helical pitch and the length of the used range of X-ray projection data used for image reconstruction is used as the parameter for the image quality of the tomographic image, which is controlled in preference to the X-ray tube current.

According to the X-ray CT apparatus 100 of the present embodiment as described above, the X-ray CT apparatus having the two-dimensional X-ray area detector of the matrix structure typified by the multi-row X-ray detector or flat-panel X-ray detector is capable of realizing such image quality of the tomographic image as to always satisfy the optimum noise standard value upon execution of the conventional scan (axial scan), the cine scan, the helical scan, the variable-pitch helical scan or the helical shuttle scan without depending on the upper limit value of the tube current of the X-ray tube even though the upper limit value is limited. The optimum image quality can be realized by assigning priorities to plural parameters that influences an image, and adjusting such plural parameters in order, based on the priorities.

Incidentally, the image reconstructing method according to the present embodiment may be a three-dimensional image reconstructing method based on a conventional known Feldkamp method. Further, another three-dimensional image reconstructing method may be adopted. Alternatively, two-dimensional image reconstruction may be used.

Although the present embodiment has been described based on the helical scan, similar effects can be brought about even in the case of the conventional scan (axial scan) and the cine scan.

Although the present embodiment has described the case in which the scanning gantry 20 is not tilted, similar effects can be brought about even in the case of a so-called tilt scan which is carried out in a state in which the scanning gantry 20 is tiled.

Although the present embodiment has described the case in which the X-ray projection data acquisition is not synchronized with the biological signal, similar effects can be brought about even when synchronization with a biological signal, particularly, a cardiac signal is taken.

Although the present embodiment has described the X-ray CT apparatus having the two-dimensional X-ray area detector of the matrix structure, which is typified by the multi-row X-ray detector or the flat panel X-ray detector, similar effects can be brought about even in the case of an X-ray CT apparatus having a one-row X-ray detector.

Incidentally, in the present embodiment, the cradle 12 of the scanning table 10 is moved in the z-direction thereby to realize the helical scan, the variable-pitch helical scan and the helical shuttle scan. However, similar effects can be brought about even by moving the scanning gantry 20 or the rotating section 15 lying inside the scanning gantry 20 relative to the cradle 12 of the scanning table 10.

In the present embodiment, the row-direction (z-direction) filters different in coefficient every row are convolved in the direction of the rows of X-ray projection data subjected to the pre-process or beam hardening process, of the respective channels to adjust variations in image quality, thereby providing uniform slice thickness for each row, preventing the occurrence of artifacts and realizing the quality of an image low in noise. Although various z-direction filter coefficients are considered therefor, any can bring about similar effects.

Although the present embodiment has described the medical X-ray CT apparatus, it can be applied even to an X-ray CT-PET apparatus, an X-ray CT-SPEC apparatus and the like combined with an industrial X-ray CT apparatus or other apparatus.

The invention claimed is:

1. An X-ray CT apparatus comprising:
an X-ray tube;
an X-ray detector positioned with respect to the X-ray tube;
an X-ray data acquisition device configured to acquire X-ray projection data by performing a scan including irradiating X-rays to a subject from the X-ray tube and transmitting the X-rays through the subject to the X-ray detector, the X-ray tube and the X-ray detector being rotated around the subject with respect to an axis extending along a Z-direction that is a body axis direction of the subject;
an image reconstructing device configured to reconstruct the X-ray projection data acquired by the X-ray data acquisition device to obtain a tomographic image; and
an imaging or scanning condition setting device configured to set a plurality of parameters as a condition for obtaining the tomographic image, the plurality of parameters including an X-ray tube current value, the imaging or scanning condition setting device comprising:
a first setting device configured to:
obtain a plurality of desired values of the X-ray tube current value corresponding to a plurality of X-ray irradiation positions, the plurality of desired values facilitate maintaining image noise of the tomographic image substantially constant in the Z-direction; and
set the plurality of desired values of the X-ray tube current value within a predetermined range; and
a second setting device configured to:
set a desired value of the X-ray tube current value to be smaller than a first value of the X-ray tube current value obtained by the first setting device, the first value corresponding to an X-ray irradiation position at which the X-ray tube current value is not within the predetermined range; and
set at least one parameter of the plurality of parameters to a desired value corresponding to the X-ray irradiation position at which the X-ray tube current value is not within the predetermined range to facilitate maintaining the image noise of the tomographic image substantially constant in the Z-direction, the at least one parameter different than the X-ray tube current value.

2. The X-ray CT apparatus according to claim 1, wherein said second setting device is configured to set the desired value of the X-ray tube current value to be constant in an area in which the at least one parameter is set to the desired value corresponding to the X-ray irradiation position.

3. The X-ray CT apparatus according to claim 1, wherein said second setting device is configured to set the desired value of the X-ray tube current value to be smaller than a second X-ray tube current value in an area in which the at least one parameter is set to the desired value corresponding to the X-ray irradiation position, and the second X-ray tube current value is adjusted preferentially to obtain a desired image quality characteristic.

4. The X-ray CT apparatus according to claim 1, wherein said second setting device is configured to set the desired value of the X-ray tube current value to a value accompanied with a parameter set to the desired value in an area in which the at least one parameter is set to the desired value corresponding to the X-ray irradiation position.

5. The X-ray CT apparatus according to claim 1, wherein said second setting device is configured to set the at least one parameter to the desired value corresponding to the X-ray irradiation position according to a speed of travel of the subject in the Z-direction.

6. The X-ray CT apparatus according to claim 1, wherein the at least one parameter includes a distance between coordinate positions in the body axis direction of one of an axial scan, a cine scan, and a helical scan.

7. The X-ray CT apparatus according to claim 1, wherein the at least one parameter includes a parameter in use for an image space z-direction filtering process used in the image reconstructing device.

8. The X-ray CT apparatus according to claim 1, wherein the at least one parameter includes a parameter in use for a projection data space row-direction filtering process used in the image reconstructing device.

9. The X-ray CT apparatus according to claim 1, wherein the at least one parameter includes a parameter in use for a projection data space channel-direction filtering process used in the image reconstructing device.

10. The X-ray CT apparatus according to claim 1, wherein the at least one parameter includes a parameter in use for a projection data space view-direction filtering process used in the image reconstructing device.

11. The X-ray CT apparatus according to claim 1, wherein the at least one parameter includes an image reconstruction parameter used in the image reconstructing device.

12. The X-ray CT apparatus according to claim 1, wherein the plurality of parameters are set according to priorities assigned thereto by said imaging or scanning condition setting device.

13. The X-ray CT apparatus according to claim 1, wherein said imaging or scanning condition setting device further comprises a device configured to set one of the X-ray tube current value to the desired value and the least one parameter to the desired value based on a size of a plane of the tomographic image.

14. The X-ray CT apparatus according to claim 1, wherein the imaging or scanning condition setting device further comprises a device configured to set one of the X-ray tube current value to the desired value and the at least one parameter to the desired value such that a standard deviation in one of a vicinity of a center at a tomographic image plane and a vicinity of a region of interest becomes constant.

15. The X-ray CT apparatus according to claim 1, wherein the scan of the X-rays is one of a variable-pitch helical scan and a helical shuttle scan.

16. The X-ray CT apparatus according to claim 1, wherein the scan of the X-rays is stopped in the body axis direction of the subject.

17. The X-ray CT apparatus according to claim 1, further comprising a display device configured to display a change in a parameter value in the body axis direction.

18. The X-ray CT apparatus according to claim 17, wherein the desired values corresponding to the X-ray irradiation position are calculated based on a result of a scout scan for setting scan conditions, and
wherein said display device is configured to display a change in the parameter value in association with an image of the subject obtained by the scout scan.

19. The X-ray CT apparatus according to claim 1, wherein the at least one parameter is a helical pitch used for a helical scan.

20. An X-ray CT apparatus comprising:
an X-ray tube;
an X-ray detector positioned with respect to the X-ray tube;
an X-ray data acquisition device configured to acquire X-ray projection data by performing a scan including irradiating X-rays from the X-ray tube and transmitting the X-rays through the subject to the X-ray detector, the X-ray tube and the X-ray detector rotatable around the subject with respect to a body axis direction of the subject;
an image reconstructing device configured to reconstruct the X-ray projection data acquired by the X-ray data acquisition device to obtain a tomographic image; and
an imaging or scanning condition setting device configured to set a plurality of parameters as a condition for obtaining the tomographic image, the plurality of parameters including an X-ray tube current value, the imaging or scanning condition setting device comprising:
a first setting device configured to:
obtain a plurality of desired values of the X-ray tube current value corresponding to a plurality of X-ray irradiation positions, the plurality of desired values facilitate maintaining image noise of the tomographic image substantially constant in a view-direction; and
set the plurality of desired values of the X-ray tube current value within a predetermined range; and
a second setting device configured to:
set a desired value of the X-ray tube current value to be smaller than a first value of the X-ray tube current value obtained by the first setting device, the first value corresponding to an X-ray irradiation position at which the X-ray tube current value is not within the predetermined range; and
set at least one parameter of the plurality of parameters to a desired value corresponding to the X-ray irradiation position at which the X-ray tube current value is not within the predetermined range to facilitate maintaining the image noise of the tomographic image substantially constant in the view-direction, the at least one parameter different than the X-ray tube current value.

21. The X-ray CT apparatus according to claim 20, wherein the at least one parameter is a helical pitch used for a helical scan.

* * * * *